(12) United States Patent
Haselton et al.

(10) Patent No.: US 10,578,615 B2
(45) Date of Patent: Mar. 3, 2020

(54) LOW RESOURCE METHOD AND DEVICE FOR DETECTING ANALYTES

(71) Applicant: Vanderbilt University, Nashville, TN (US)

(72) Inventors: Rick Haselton, Nashville, TN (US); David Wright, Nashville, TN (US); Nick Adams, Nashville, TN (US); Keersten Ricks, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 309 days.

(21) Appl. No.: 15/302,553

(22) PCT Filed: Apr. 8, 2015

(86) PCT No.: PCT/US2015/024971
§ 371 (c)(1),
(2) Date: Oct. 7, 2016

(87) PCT Pub. No.: WO2015/157448
PCT Pub. Date: Oct. 15, 2015

(65) Prior Publication Data
US 2017/0030903 A1 Feb. 2, 2017

Related U.S. Application Data

(60) Provisional application No. 61/976,907, filed on Apr. 8, 2014.

(51) Int. Cl.
*B01L 3/00* (2006.01)
*G01N 33/558* (2006.01)
(Continued)

(52) U.S. Cl.
CPC ...... *G01N 33/558* (2013.01); *B01L 3/502715* (2013.01); *B01L 9/527* (2013.01);
(Continued)

(58) Field of Classification Search
None
See application file for complete search history.

(56) References Cited

U.S. PATENT DOCUMENTS 6,136,549 A * 10/2000 Feistel ............. G01N 33/54333
422/423
6,981,522 B2 * 1/2006 O'Connor ............... B01F 5/064
137/559
(Continued)

FOREIGN PATENT DOCUMENTS

EP       2641975 A1 *  9/2013 ......... G01N 35/1079
WO    WO/2013/0183678    7/2013
WO    WO/2007/0244381   10/2015

OTHER PUBLICATIONS

International Search Report and Opinion issued in PCT Application No. PCT/US2015/024971 dated Sep. 14, 2015.
(Continued)

*Primary Examiner* — Erik B Crawford
(74) *Attorney, Agent, or Firm* — Parker Highlander PLLC

(57) ABSTRACT

Systems and methods are described for isolation, separation and detection of a molecular species using a low resource device for processing of samples. Methods include isolation, separation and detection of whole cells.

18 Claims, 13 Drawing Sheets

(51) Int. Cl.
*G01N 33/543* (2006.01)
*B01L 9/00* (2006.01)
*G01N 35/00* (2006.01)

(52) U.S. Cl.
CPC . *G01N 33/54326* (2013.01); *G01N 33/54333* (2013.01); *G01N 35/0098* (2013.01); *B01L 2200/0668* (2013.01); *B01L 2300/0672* (2013.01); *B01L 2300/087* (2013.01); *B01L 2300/0867* (2013.01)

(56) References Cited

U.S. PATENT DOCUMENTS

| | | | |
|---|---|---|---|
| 7,646,484 | B2 | 1/2010 | Pesach et al. |
| 7,872,734 | B2 | 1/2011 | Braig et al. |
| 2004/0229299 | A1* | 11/2004 | Badal .............. G01N 33/542 435/7.23 |
| 2005/0227370 | A1* | 10/2005 | Ramel .............. C12Q 1/00 436/514 |
| 2007/0244381 | A1 | 10/2007 | Robinson et al. |
| 2009/0215072 | A1* | 8/2009 | McDevitt .......... G01N 21/6428 435/7.1 |
| 2010/0024530 | A1* | 2/2010 | Hopkins, II ........ B01L 3/5023 73/64.56 |
| 2010/0317093 | A1* | 12/2010 | Turewicz ............ B01L 3/50273 435/287.2 |
| 2011/0003303 | A1* | 1/2011 | Pagano ............ B01L 3/502761 435/6.19 |
| 2012/0070833 | A1* | 3/2012 | Wang ................. B01L 3/502776 435/6.11 |
| 2013/0017538 | A1* | 1/2013 | Ionescu-Zanetti ...... B03C 1/288 435/6.11 |
| 2013/0183678 | A1 | 7/2013 | Haselton |

OTHER PUBLICATIONS

Bell and Peeling, "Evaluation of rapid diagnostic tests: malaria." *Nature Reviews Microbiology*, 4, S34, 2006.

Davis et al., "Low-resource method for extracting the malarial biomarker histidine-rich protein II to enhance diagnostic test performance." *Analytical Chemistry*, 84, 6136-6142, 2012.

Laishram et al., "The complexities of malaria disease manifestations with a focus on asymptomatic malaria." *Malaria Journal*, 11, 29, 2012.

Mudanyali et al., "Integrated rapid-diagnostic-test reader platform on a cellphone." *Lab on a chip*, 12, 2678-2686, 2012.

Murray and Bennett, "Rapid Diagnosis of Malaria" *Interdisciplinary Perspectives on Infectious Diseases*, 2009.

Murray et al., "Update on rapid diagnostic testing for malaria." *Clinical Microbiology Reviews*, 21, 97-110, 2008.

Okell et al., "Factors determining the occurrence of submicroscopic malaria infections and their relevance for control." *Nat Commun*, 3, 1237, 2012.

Shekalaghe et al., "Clinical performance of an automated reader in interpreting malaria rapid diagnostic tests in Tanzania." *Malaria Journal*, 12, 141, 2013.

Sturrock et al., "Targeting asymptomatic malaria infections: active surveillance in control and elimination." *PLoS Med*, 10, e1001467, 2013.

* cited by examiner

| Type | Bead chemistry/biomarker capture agent | Release agent | Biomarker class | Refs. |
|---|---|---|---|---|
| Direct catch and release | Ni-NTA-functionalized beads bind histidine rich biomarkers directly | imidazole | pfHRPII protein | (1,2) |
| | Oligo-(dT)-functionalized beads bind biomarkers with poly(A) tails directly | low pH, heat | mRNA | (3,4) |
| | Chitosan-functionalized beads bind negatively charged biomarkers directly | low pH, heat | DNA, RNA | (5,6) |
| Ligand-mediated catch and release | Ni-NTA-functionalized bead attached to poly-His tagged molecular recognition agent* | imidazole | proteins, nucleic acids, whole cells | (7) |
| | Oligo (dT)-functionalized bead attached to poly(A)-tagged molecular recognition agent* | low pH, heat | proteins, nucleic acids, whole cells | (3) |
| | Anti-FLAG antibody bead attached to FLAG-tagged molecular recognition agent* | excess FLAG peptide, protease | proteins, nucleic acids, whole cells | (7,8) |
| | $PPh_3$-functionalized bead attached to alkyne-derivatized molecular recognition agent* | $Fe(NO_3)_3$ | proteins, nucleic acids, whole cells | (9) |
| | Photolabile linker (o-nitrobenzyl or azobenzene group) attached to molecular recognition agent* | UV light | proteins, nucleic acids, whole cells | (10-12) |
| | pH sensitive linker (phenylboronic acid or HPEDA) | low pH | proteins, whole cells | (13,14) |

*Molecular recognition agent refers to a molecule with affinity for a particular biomarker (e.g. antibodies, aptamers, oligonucleotides)

FIG. 14

LOW RESOURCE METHOD AND DEVICE FOR DETECTING ANALYTES

This application is a national phase application under 35 U.S.C. § 371 of International Application No. PCT/US2015/024971, filed Apr. 8, 2015, which claims benefit of priority to U.S. Provisional Application Ser. No. 61/976,907, filed Apr. 8, 2014, the entire content of each of which is hereby incorporated by reference.

The invention was made with government support under Grant No. DGE 0909667 awarded by the National Science Foundation. The government has certain rights in the invention.

BACKGROUND

1. Field

The disclosure relates generally to the field of diagnostics and detection. More particularly, the disclosure relates to low resource processors for assessing molecular interactions. Specifically, the disclosure relates to a variety of lateral flow assays that employ beads with capture agents, and they processing and delivery to a chromatographic substrate. In a particular aspect, the beads are magnetic, and may employ "catch and release" chemistries. Specific devices containing multiple chambers that are in fluid connection and that facilitate the delivery of samples to commercial rapid diagnostic test cassettes that are inserted into the device. The device permits assaying for the content of a wide variety of environmental and biological samples, including whole cells.

2. Description of Related Art

The advent of point of care (POC) diagnostic tools has changed the face of healthcare in nations affected by the ongoing spread of infectious diseases (Yager et al., 2008). These underdeveloped, remote areas are often characterized by poverty, absent or intermittent electricity, hot and humid environmental conditions as well as a lack of skilled clinicians. Lateral flow immunochromatographic rapid diagnostic tests (RDTs), which operate much like a commercial pregnancy test, were developed to circumvent these challenges and bring affordable disease diagnosis to low resource areas (Murray and Bennett, 2009; Murray et al., 2008). Several advantages of RDTs include low cost, rapid time to result, and ease of use and interpretability (Bell and Peeling, 2006).

Additionally, these tests have been widely used in public health programs to aid with patient management, disease surveillance and treatment campaigns (D. Bell and M. Perkins, 2012). In 2006, over 16 million RDTs were delivered to underdeveloped nations for the detection of malaria alone (C. K. Murray and J. W. Bennett, 2009). These RDTs detect protein biomarkers of the malarial parasite. The predominant RDT biomarker indicative of *Plasmodium falciparum* infection is Histidine Rich Protein II (pfHRPII), while *Plasmodium* Lactate Dehydrogenase (pLDH) serves as a pan-specific biomarker (Murray and Bennett, 2009).

Despite the many advantages of RDTs, the changing climate of infectious disease education, prevention, and treatment has highlighted the need for improved tests. The World Health Organization (WHO) periodically reviews all malaria RDTs manufactured for diagnostic use, and sets the limit of detection for these tests at 200 parasites/μL (World Health Organization, 2011). While this limit of detection is sufficient for the diagnosis of symptomatic malaria infection many asymptomatic patients are not diagnosed and continue to be transmission reservoirs of the disease because current RDTs fail to identify these asymptomatic carriers. Additionally, poor manufacturing standards and storage conditions render many brands of malaria RDTs inoperable and unreliable (Wongsrichanalai et al., 2007). There are an estimated 60 brands and 200 types of tests manufactured for the detection of malaria, and according to the WHO, less than 10% of those tests are effective at detecting 200 parasites/μL parasite densities (Malaria Rapid Diagnostic Test Performance Results, WHO 2011. Unfortunately, tests are often acquired based on government sanctions, history of use, and cost instead of acquisition based on reliability of the brand (Bell et al., 2006). This variability in test performance, sensitivity and reliability undermines the progress made in malaria disease prevention (Gubala et al., 2011).

The inventors have recently reported the development of a low resource extraction cassette that can extract, purify and concentrate the most common malarial biomarker, *Plasmodium falciparum* Histidine Rich Protein II (pfHRPII), from a blood sample, in less than 30 minutes (Davis et al., 2012). In this study, a series of aqueous buffer solutions separated by air and oil surface tension valves were preloaded into a single length of tubing. They were able to purify the protein biomarker from blood by processing biomarker bound magnetic particles through the cassette using a handheld magnet. At least 50% extraction efficiency was demonstrated for samples with parasitemias as low as 12.5 parasites/μL and, as a result of this technique, a commercial RDT brand was qualitatively improved over 8-fold. Nonetheless, it would be useful to have a simpler design that would provide for high quality samples useful in commercial RDT devices in low resource environments.

However, even RDTs are limited to a certain extent by the nature and quality of samples being tested. For example, RDTs, including lateral flow assays (LFAs) produce more signal if more biomarkers are added, and thus are better able to detect biomarkers. Adding more patient sample to an LFA is one way to add more biomarkers; however, LFAs will not function with patient sample volumes greater than 20-40 μL (depending on the LFA size and material composition) because (i) LFA test strips have a limited capacity, and (ii) larger volumes of patient samples contain more cellular debris, which inhibit the capillarity the drives the assay. Therefore, additional solutions for these problems also would be of significant value.

SUMMARY

In one aspect, the disclosure relates to the use of mBEADS (magnetically-enabled biomarker extraction and delivery system). The major components of the mBEADS system are (i) a sample collection container; (ii) magnetic beads with biomarker capture surface chemistry, (iii) reagents to promote biomarker binding to the beads, (iv) a magnetic field gradient, (v) an LFA, biomarker release solution, and (vi) an LFA running buffer. There are four main processes that are involved in this sort of system: (1) mixing of the sample with the magnetic beads in the presence of reagent to promote biomarker binding, such as based on liquid motion (tube vortexing or rotating), bead motion (magnetic or acoustic), or both; (2) removing magnetic beads from the sample and directing the beads to the deposition pad of the LFA using a magnetic field gradient; (3) releasing the biomarkers from the beads before or after the beads are applied to the LFA using release chemistries; and (4) processing the biomarkers on the LFA using a running buffer and chemistries.

In accordance with one aspect of the present disclosure, there is a device comprising (a) a first port connected to a first chamber for receiving a removable diagnostic test (RDT) module; (b) a second port connected to a second chamber for receiving a sample, wherein the first and second chambers are in fluid connection; (c) a third port connected to a third chamber for receiving a buffer, wherein the first and third chambers are in fluid connection. The device may further comprise a magnet, such as where the magnet is positioned adjacent to a near wall of the first chamber, and the second chamber is positioned on a far wall of the first chamber. The RDT module may comprise ports that, when the RDT module is inserted into the device, align with the second and third chambers.

The second port may be configured to receive a tube. The third port may be configured to receive a pipette, a tube, or a hose. The housing for the device may be comprised of a 3D-printable polymer. The second port may comprise a means to engage a structure on the outer wall of the tube, the means and structure designed to insure proper positioning of the bottom of the tube in the second chamber. The second and third chambers may be connected such that when the tube is engaged, the RDT module is locked into the first chamber. The device may comprise an element in the second port or chamber such that insertion of the tube results in introduction of an opening in the tube.

In another embodiment, there is provided a method of performing a diagnostic assay comprising (a) introducing a sample suspected of comprising an analyte into a tube that contains magnetic particles carrying a binding ligand for the analyte; (b) providing a device comprising: (i) a first port connected to a first chamber for receiving a removable diagnostic test (RDT) module; (ii) a second port connected to a second chamber for receiving the sample, wherein the first and second chambers are in fluid connection; (iii) a third port connected to a third chamber for receiving a buffer, wherein the first and third chambers are in fluid connection; (c) introducing the RDT module into the first port connected to the first chamber such that the removable diagnostic test module is disposed in the first chamber; (d) introducing the sample into the second port connected to the second chamber; (e) applying a magnetic field to the sample when disposed in the second chamber such that the magnetic particles contact a surface in the RDT module; (f) introducing a buffer into the third port connected to the third chamber, wherein the buffer contacts a surface in the RDT module and moves toward the second chamber, such that the buffer contacts the magnetic particles disposed on the surface in the RDT module; and (g) detecting an analyte released from or transported by the magnetic particles by application of the buffer.

The sample may be introduced into the second port and second chamber in a tube, and an opening in the tube may be created prior to or during the introduction of the tube into the second port and second chamber. The opening may be created by removing a portion of the tube or a cap on the tube prior to introduction into the second port, the sample being initially retained in the tube by surface tension at the opening. Alternatively, the opening may be created by introducing the tube into the second port. The magnetic field may be a static field emanating from a magnet located in the device. Alternatively, the magnetic field may be a user applied field emanating from a magnet inserted into the device or external to the device. The housing for the device may be comprised of a 3D-printable polymer.

The second port may comprise a means to engage a structure on the outer wall of the tube, the means and structure designed to insure proper positioning of the bottom of the tube in the second chamber. The support may be a lateral flow test strip. The second and third chambers may be connected such that when the tube is engaged, the RDT module is locked into the first chamber. The analyte may be selected from a pathogen antigen, and antibody, an environmental toxin, a drug, or a cancer marker. The binding ligand maybe an antibody, a carbohydrate, or a metal. The buffer may release the antigen from the magnetic bead by a change in pH, a change in ionic strength, or competitive binding for the ligand or the analyte, and further may transport the antigen after release into a reaction zone on the RDT module. The buffer may transport the magnetic particle into a reaction zone on the RDT module, and the method may further comprise detecting the magnetic particle or an agent located on the surface of the magnetic particle.

In another embodiment, there is provided a method of purifying an analyte from a sample comprising (a) mixing of a fluid sample containing an analyte with a population of magnetic beads, wherein the magnetic beads comprise a reagent that binds to the analyte; (b) incubating the sample and magnetic beads under conditions promoting binding of analyte and reagent; and (c) removing the magnetic beads from the sample using a magnetic field gradient. Step (b) may comprise mixing of the sample by motion of a container in which the sample is disposed, or by motion of beads within a container in which the sample is disposed, such as motion induced by a magnetic field selected from a non-uniform field, a static field and a fluctuating field. The analyte may be retained on the magnetic beads by "catch and release chemistries." The method may further comprise delivering the magnetic particles to an RDT device as described above.

Step (c) may comprise withdrawal of magnetic beads from a container in which the sample is disposed through an aperture regulated by an air or gas valve that permits little or no sample other than the magnetic beads to pass, such as where the container is a tube, and in particular a tube having a removable bottom covering the aperture prior to step (c). The tube may be moved past a magnetic field, resulting in withdrawal of the magnetic beads from the container, or the magnetic field may be moved past the tube, resulting in withdrawal of the magnetic beads from the container. The tube may be rotated adjacent to a magnetic field, resulting in withdrawal of the magnetic beads from the container. Withdrawal of magnetic beads may result in direct deposition of the magnetic beads on a lateral flow assay substrate, optionally followed by releasing the analyte from the magnetic beads, and optionally further detecting the analyte.

The withdrawal of the magnetic beads may results in deposition onto an inert hydrophobic surface, where the magnetic beads are retained prior to detection or further processing, and such method may further comprise releasing the analyte from the magnetic beads, and then removing the hydrophobic surface while a magnetic field is positioned to prevent movement of the magnetic beads, resulting in deposition of the magnetic beads onto a lateral flow assay substrate, optionally followed by detecting the analyte.

The withdrawal of the magnetic beads may result in deposition on a surface or into a chamber for further processing. The chamber may be a pipette, and the analyte may be released from the magnetic beads in the pipette, and then expelled from the pipette on to a lateral flow assay support. The chamber may be a pipette, and the analyte may be released from the magnetic beads in the pipette, and then expelled from the pipette an inert hydrophobic surface, where the magnetic beads are retained prior to detection or further processing.

The method may further comprise transporting the magnetic beads through one or more chambers containing the sample and/or processing or detection fluids by subjecting the one or more chambers comprising the magnetic beads to a magnetic field. The magnetic field may be induced by two magnets on opposing sides of the one or more chambers. One or more chambers may be moved relative to the magnetic field, or the magnetic field may be moved relative to the one or more chambers. The magnetic field may be an opposed hemi-spherical magnetic field. The magnetic field gradient may be produced by a permanent magnet or an electromagnet.

In yet a further embodiment, there is provided a method of purifying an analyte from a sample comprising (a) mixing of a fluid sample containing an analyte with a population of high density beads, as compared to the density of the sample, wherein the high density beads comprise a reagent that binds to the analyte; (b) incubating the sample and high density beads under conditions promoting binding of analyte and reagent; and (c) removing high density beads from the sample using gravity or centrifugal force. High density may be defined as greater than 1 gm/cm$^3$.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 9A) The magnet moves the beads along the side and the tube/cylinder they are deposited as they move past the lip of the tube wall. (FIG. 9B) Same idea but tube moved instead of magnet. (FIG. 9C) Shows a rotating tube with a hole which passes magnetic beads when aligned with magnet. Note: permanent magnets not required most could also be done using an electromagnet though probably weaker; do have the advantage that fields can be easily modulated by switching coils on and off (that is without the need to move the permanent magnets); had an accelerator design that we thought not feasible because of current drains FIG. 10—mBEADS hydrophobic pull-tabe design. Transfer of magnetic beads to the surface of a removable sliding hydrophobic surface. (1) Sample is mixed with magnetic beads then the tube is touched to surface of hydrophobic tab and withdrawn. The beads left on hydrophobic surface with minimal fluid volume through the surface tension valve at the tip of the tube. (2) The tab is removed and beads remain above the magnet beneath the LFA and are deposited on the lateral flow strip when the tab is removed completely; running buffer added upstream to the lateral flow strip.

(FIG. 13A) Direct biomarker catch and release. The interaction between the biomarker capture agent on the bead surface and the biomarker of interest is disrupted using a biomarker release agent. Examples include: i) Ni-NTA beads binding pfHRPII biomarkers and being released by imidazole and ii) oligo (dT) beads binding mRNA molecules and being released by heat. (FIG. 13B) Ligand-mediated biomarker catch and release. The interaction between the ligand capture agent and the biomarker capture ligand is disrupted using a ligand release agent. In this mechanism, the biomarker capture ligand and biomarker are released as a complex. Examples include: i) Ni-NTA beads binding to poly(His)-tagged antibodies for a biomarker of interest and being released by imidazole and ii) oligo (dT) beads binding to poly(A)-tagged antibodies and being released by heat.

FIG. 14—"Catch and Release" chemistries for mBEADS.

(FIG. 15A) Single magnet on one side of the sample tube. In this magnetic orientation, the magnetic beads are packed onto the inner wall of the tube. This orientation works well for moving the magnetic beads down the tube or for retaining the magnetic beads while moving the fluids through the tube. This orientation does not work well for maximizing interactions with the surface of the magnetic beads and the fluid while mixing the magnetic beads with the sample. (FIG. 15B) Two attracting magnets on opposite sides of the sample tube. In this magnetic orientation, the magnetic beads are distributed in a loose column inside of the tube. This orientation works well for moving the magnetic beads down the tube, for retaining the magnetic beads while moving the fluids through the tube, and for maximizing interactions with the surface of the magnetic beads and the fluid while mixing the magnetic beads with the sample. (FIGS. 15C-D) Two additional view of single versus dual magnet embodiments. (FIG. 15E) Two magnet orientation in opposed hemispherical design.

DESCRIPTION OF ILLUSTRATIVE EMBODIMENTS

Figure 1:
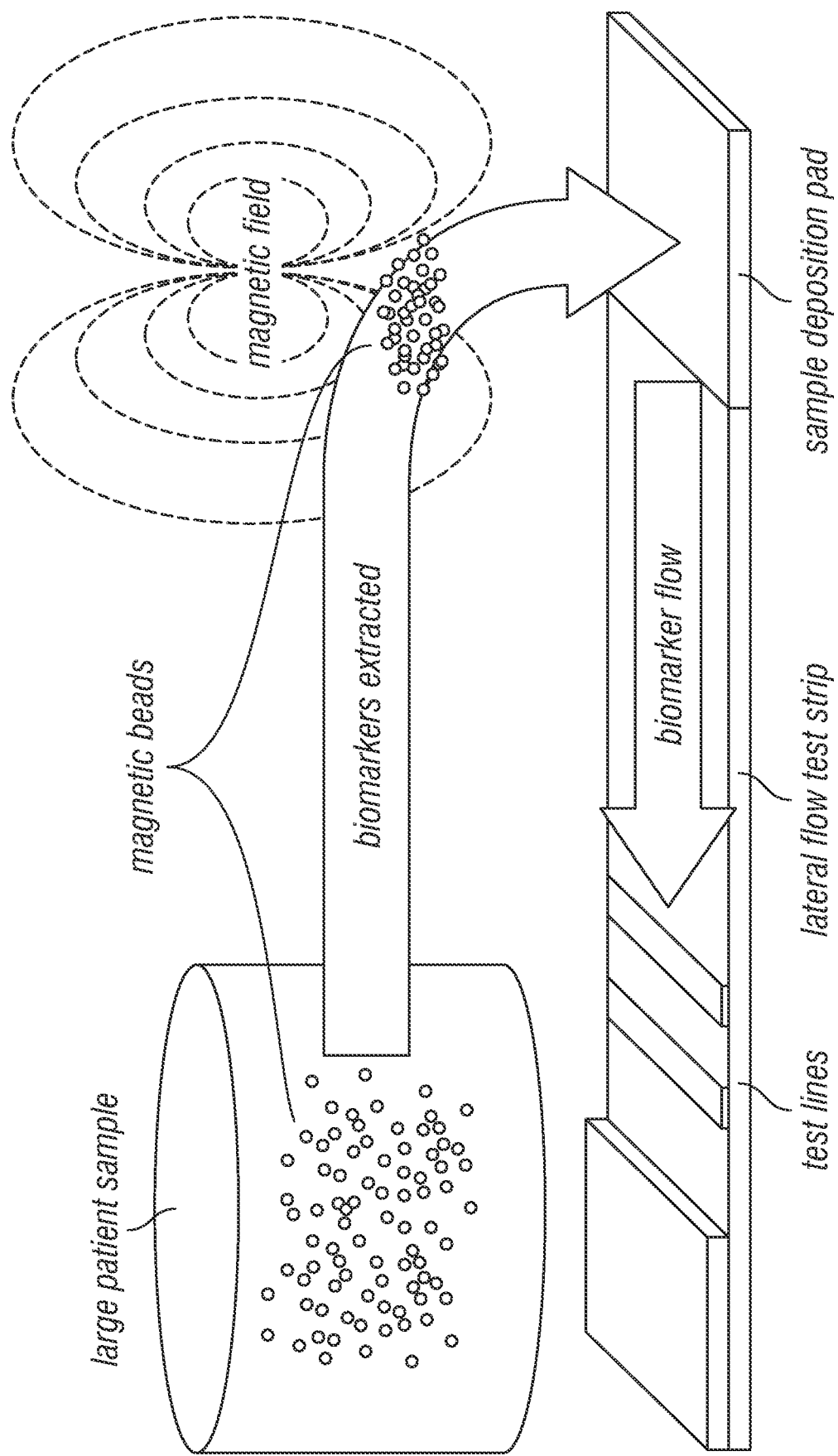
FIG. 1—General concept for concentrating patient sample biomarkers onto lateral flow assay test strips using the magnetically-enabled biomarker extraction and delivery system (mBEADS). Biomarkers are concentrated from sample volumes that are too large to be added directly to the test strip (50 μL-10 mL) using magnetic beads (test strips have an upper limit of roughly 40 μL of sample volume before becoming nonfunctional). While the patient sample is mixing with the magnetic beads, biomarkers are captured onto magnetic beads by binding to molecular recognition agents that are attached to their surface. Biomarker-bound beads are mixed and/or separated from the bulk solution using a magnetic field gradient to direct the movement of the beads. Biomarkers are released from the surface of the beads using "catch and release" chemistries either directly onto the sample deposition pad of the lateral flow test strip or in a secondary chamber prior to being applied to the lateral flow test strip. Lateral flow buffer is used to carry the biomarkers up the test strip to the test lines.

Here, the inventors describe variety of methods for improving existing rapid diagnostic tests for the detection of antigens, including pathogens such as malaria. In general, the assays involve a combination of pre-processing followed by a lateral flow assay. The major components involve sample collection, magnetic beads with biomarker capture surface chemistry and reagents to promote biomarker binding to the beads, a magnetic field gradient, and various biomarker release and separation solutions. In general, one mixes a sample with magnetic beads to promote biomarker binding, then removes magnetic beads from the sample and deposits them on a pad of a LFA where the biomarkers are released from the beads followed by processing and detection of the biomarkers on the LFA surface.

In one aspect, using an RDT device, regardless of the panel detection scores assigned to the selected brands by the World Health Organization, the inventors found five of six brands could be improved to detect parasitemia within submicroscopic levels of infection—a level of diagnosis that RDTs have traditionally been unable to achieve. Both the visual signal and limit of detection gained a 4-fold and in some cases 100-fold enhancement. Limits of detection, after extraction, were estimated to be as low as 3 parasites/µL for two brands. Several labs are currently developing cell phone RDT readers, which use an algorithm similar to that described here to convert the visual test signal to a quantitative one (Mudanyali et al., 2012; Shekalaghe et al., 2013). By combining the inventors' extraction technology with these developing resources, the positive impact of RDTs for malaria control could become an important tool for diagnosing symptomatic and asymptomatic carriers. With these advances in RDT technology, rapid, affordable, point-of-care diagnostics will continue to be at the forefront of malaria eradication efforts in underdeveloped nations.

In the present study, the inventors describe the utility of this extraction cassette for the improvement of a wide range of RDT brands of variable performance. Additionally, this improvement is quantitated at parasitemias below the 200 parasites/µL regime. Finally, they describe the effect of individual donor samples on low, medium and high performing RDT brands at various parasite loads. In addition, the inventors provide several methods using mBEADS (or magnetically-enabled biomarker extraction and delivery system) that improve the function of LFAs and RDTs, for example, by (a) extracting and concentrating biomarkers from patient sample volumes that would otherwise be too large to be applied to an LFA, and (b) leaving behind the bulk sample containing the unwanted cellular debris, proteins, nucleic acids, and other inhibitory material. These and other aspects of the disclosure are described in greater detail below.

A. TUBE BASED PRE-PROCESSING DEVICE

In one embodiment, pre-processing of samples will employ continuous tubing as the basis for creating a plurality of chambers. The chambers are, in essence, liquid pockets that are maintained separate from each other by the use of surface tension valves, which are fluid or gaseous agents interspersed between the fluid pockets. The device may also include predisposed therein particles for use in binding analytes that are introduced into the device.

1. Tubing

Central to the design of this device is the establishment of a series of solutions arrayed along a tube each separated from the next by a surface tension valve. Only tubing of sufficiently small diameter will allow for a stable arrangement of the fluids and valves. Tubing of diameter greater than about 4 mm will not support stable valve formation. Therefore an important physical property of this component is its diameter.

The tubing may be made of a variety different materials including glass, polymers or metal. The tubing should be made of, or internally coated with, a polymer that permits formation of surface tension valves, discussed further below. It is also desirable to have tubing with low surface energy, meaning that it is non-binding for proteins, and also hydrophobic. These properties of the tubing material affect the stability of the arrayed solutions and therefore the diameter of the tubing that is useable. Lower surface energy generally will require a tubing of smaller diameter to permit stable valve formation. Typical surface energy values for glass, silanized glass, polystyrene, Teflon and some types of fluorinated ethylene polypropylene Tygon tubing are in the range of 10-50, 10-30, 15-30, 20-30, 5 mN/m, including 10, 15, 18.5, 20, 25, 30, 35, 40, 45 and 50 mN/m.

A particular type of tubing is Tygon® tubing, which is a brand name for a variety of flexible tubing. Tygon® is a registered trademark of Saint-Gobain Corporation. Tygon® Tubing is used in many markets including food and beverage, chemical processing, industrial, laboratory, medical, pharmaceutical, and semiconductor processing. There are many formulations of clear, flexible, Tygon® tubing. The chemical resistance and physical properties vary among the different formulations, but the tubing generally is considered resistant to almost any chemical attack.

Several formulations of Tygon® are Class VI approved and can be used in either surgical procedures or pharmaceutical processing. Medical versions include the following:

Tygon® Medical/Surgical Tubing S-50-HL—Characterized to the latest ISO 10993 standards and FDA guidelines for biocompatibility. This material is non-toxic, non-hemolytic, and non-pyrogenic. This formulation is used in minimally invasive devices, dialysis equipment, for bypass procedures, and chemotherapy drug delivery.

Tygon® Medical Tubing S-54-HL was introduced in 1964 for use in medical applications. This material can be used in catheters, for intravenous or intra-arterial infusion and other surgical uses. Tygon S-54-HL can also be fabricated into cannulae or protective sheath products using thermoforming and flaring techniques.

Pharmaceutical Tygon includes:

Tygon® LFL (Long Flex Life) pump tubing is non-toxic clear tubing with broad chemical resistance. It is often used in product filtration and fermentation and surfactant delivery.

Tygon® 2275 High Purity Tubing is a plasticizer-free material that is often used in sterile filling and dispensing systems and diagnostic equipment. This formulation is also considered to have low absorption/adsorption properties which minimizes the risk of fluid alteration.

Tygon® 2275 I.B. High-Purity Pressure Tubing is plasticizer-free and is reinforced with a braid for use with elevated working pressures.

Tygon® chemfluor FEP is a non-protein binding tubing which contains no additives or plasticizers. FEP stands for fluorinated ethylene propylene.

Peristaltic applications include the following:

Tygon® R-3603 Laboratory Tubing is commonly used in university laboratories. It is often used in incubators, hoods and as a replacement for rubber tubing for Bunsen burners. This material is produced in vacuum sizes and can withstand a full vacuum at room temperature.

Tygon® R-1000 Ultra-Soft Tubing is used in general laboratory applications. It is the softest of the Tygon formulations with a durometer hardness of Shore A 40 (ASTM Method D2240-02). Because of the low durometer of this material it is often used in low-torque peristaltic pumps.

Tygon® LFL (Long Flex Life) Pump Tubing, Tygon® 3350, Tygon® S-50-HL Medical/Surgical Tubing, Tygon® 2275 High Purity Tubing, and Tygon® 2001 Tubing are also used in peristaltic pump applications.

Other Types of Tubing Include the Following.

Silicone Tubing (LPS), which is the most commonly used peristaltic pump tubing. It provides the longest service life and good chemical compatibility for aqueous solvents. Silicone tubing can be autoclaved a single time using a wet cycle. Vinyl Tubing (LPV) has the lowest per-foot cost of the available peristaltic pump tubings. It generally has only fair compatibility for most aqueous solvents and does not have a good tolerance for organic solvents. It has only about one-third the service live of silicone tubing in a peristaltic pump. Vinyl tubing should not be autoclaved or exposed to temperatures above 80° C. Fluoroelastomer Tubing (LPF) is both the most chemically inert and the shortest lived peristaltic pump tubing. It can even withstand halogenated solvents for a limited time. Its service life is only about one-twentieth that of silicone tubing in a peristaltic pump. Like silicone tubing, fluoroelastomer tubing can be autoclaved a single time using a wet cycle. Teflon® Tubing (HPT) is the most inert of all the tubing we manufacture. It can withstand nearly any solvent used in a modern laboratory, from distilled water to methylene chloride. Its excellent thermal characteristics allow it to be autoclaved repeatedly. After autoclaving Teflon tubing should not be used for fluid transport until it has cooled. Polyethylene Tubing (HPP) is an inexpensive alternative to Teflon tubing. Like Teflon tubing, polyethylene can handle pressure significantly higher than any of other flexible tubings. Polyethylene does not have the thermal stability of Teflon so it should not be autoclaved; it can, however, be sterilized ethylene oxide.

2. Chambers

The present inventors have designed processing chambers, equipped with gas/fluid valves, that permit the passage of particles into and out of the chambers without substantial loss of liquids, and preservation of each compartment's integrity. In a particular embodiment, the processing chambers are configured to provide down to nanoliter volumes. Reaction, processing, hybridization, and analysis steps can be conducted in a series of separate chambers. In general, the chambers contain aqueous liquids that contain various chemical and biological species, such as salts, dyes, labels and other chemical species.

Reaction Chambers.

One type of chamber is a reaction chamber. In a reaction chamber, the analyte associate with the reactant on the surface of the particle. Such a reaction chamber would be unnecessary in an embodiment where the particles are mixed with a sample prior to introduction into the device. Generally, a reaction chamber will provide suitable conditions under which the reactant on the particle and the analyte may interact. The reaction chamber may optionally include agents to inhibit non-specific interactions or to stabilize interactions once achieved.

Processing Chambers.

A variety of different types of chambers may be used in accordance with the present invention. It also is possible, where convenient, to have a series of processing chambers. A processing chamber may also be reused in the sense that the flow of the particles may be reversed so that a given chamber is used more than once. The present invention may also utilize multiple processing chambers where different solutions included therein.

One example processing chamber is a pretreatment chamber. It is often the case that reactants, samples or particles will be "pretreated" in such a way as to ensure that the ensuing reaction with the target has a high degree of fidelity, i.e., minimize non-specific attachment. A classic example is of a pretreatment is a "blocking" reaction. Non-specific protein-protein interactions by inhibited by pretreating a substrate with a non-specific protein such as BSA. Similarly, non-specific DNA reactions can be reduced by incubating the probe with a "random" DNA known to lack homology with the probe. In this case, a pretreatment chamber will proceed a reaction chamber.

Another important step when assessing the reaction of biomolecules is to remove non-specifically bound molecules from the reactant. Though achieving the same goal as pretreatment, washing takes place after the exposure of reactant to target. Typically, wash solutions comprise a buffer similar to that used in the target solution, but lacking the target itself. Occasionally, it will be desirable to alter the chemical properties of the wash solution by, for example, changing the salt concentration or pH. Wash chambers would follow a reaction chamber.

An additional chamber may be included into which the species of interest is released during the final extraction process. This chamber's function is to provide the elution step of many extraction processes. This chamber may also effectively function as a concentrating chamber since if its volume is sufficiently small compared to the original sample volume, the number of molecular targets will be higher than in the initial sample, thus effectively concentrating this species.

In some embodiments, it may be desirable to recursively amplify signals relating to binding of target analytes to reactants, or to generate more target for reaction. There are a variety of mechanisms for accomplishing this. However, a common feature will be the need for one or more chambers, prior to or following a reaction chamber, which effect the necessary steps to achieve the amplification.

Finally, in order to increase the efficiency of the process, particles may be retrieved from downstream of processing chambers and be returned to an upstream reaction or processing chamber, either by extraction and reintroduction or by reversal of the transport mechanism (e.g., centrifugal force, density or magnetic). By repeating the reaction and/or processing steps, one can increase both the signal and specificity of binding and detection.

3. Surface Tension Valves

An important aspect of the invention is the use of surface tension valves to separate the tubing into discrete chambers. These surface tension valves allow for the selective passage of beads onto a lateral flow assay surface while retaining most of the sample in the pre-processing chamber or device. A typical lateral flow strip processed by capillary action is useful with only a limited volume of fluid, around 40 µl. Since a better outcome in terms of sensitivity is achieved by delivering more biomarkers gathered from a larger sample, this bigger volume (which cannot be applied to the lateral flow strip) needs to be stripped of the relevant biomarkers by functionalized magnetic beads, and then only the magnetic beads transferred through the air/liquid surface tension valve. This limits the volume of liquid transferred to a very small volume on the order of microliters per milligrams of beads, and thus does not disrupt the normal operation of a lateral flow strip.

In essence, the surface tension valve is simply a nonreactive gas or liquid that separates various sections of the device by creating a stable interface with the fluids that make up the various chambers. Important aspects of the gas or liquid include low vapor pressure or low surface tension, which are defined as having a vapor pressure significantly less than 1 kPa and a surface tension between 2 and 100 mN/m, including about 72 for air/water, about 50 for water/mineral oil, and about 3.3 for benzyl alcohol/water (values are from Handbook of Organic Solvents) (Lide, 1995) (incorporated by reference). Examples of appropriate gases include air, carbon dioxide, nitrogen, argon, helium, or sulfur hexafluoride. Liquids include Mineral oil, Dodecane, 1-Dodecene, Tridecane, Methyloleate, Acetophenone, Propyl Benzoate, or 1-Methylnaphthalene. Also, addition of certain materials can alter the surface tension interface, e.g., Tween® can lower the surface tension.

B. LATERAL FLOW ASSAYS

Much of the following describes various aspects of what are generally termed "lateral flow assays," or LFAs. Lateral flow assays, also known as lateral flow immunochromatographic assays, are simple devices intended to detect the presence (or absence) of a target analyte in sample (matrix) without the need for specialized and costly equipment, though many lab based applications exist that are supported by reading equipment. Typically, these tests are used as low resources medical diagnostics, either for home testing, point of care testing, or laboratory use. A widely spread and well known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays.

C. RAPID DIAGNOSTIC TEST (RDT) GARAGE AND DEVICE FOR USE THEREWITH

In one aspect, the present disclosure provides a rapid diagnostic test (RDT) garage. An RDT garage comprises a housing designed to receive an RDT cassette, of which there are numerous commercial version testing for a variety of diseases. RDT cassettes are generally characterized by a housing that contain a substrate onto which a sample is applied. Reactants are located on the substrate permitting binding and detection of analytes from the samples, along with positive and negative controls. Examples include Paracheck Pf (Orchid Biomedical Systems), One Step Pf (Blue Cross Biomedical), ParaHit Pf (Span Diagnostics), ParaHit Total (Span Diagnostics), ICT Dual (ICT Diagnostics) and ICT Pf (ICT Diagnostics).

Figure 7:
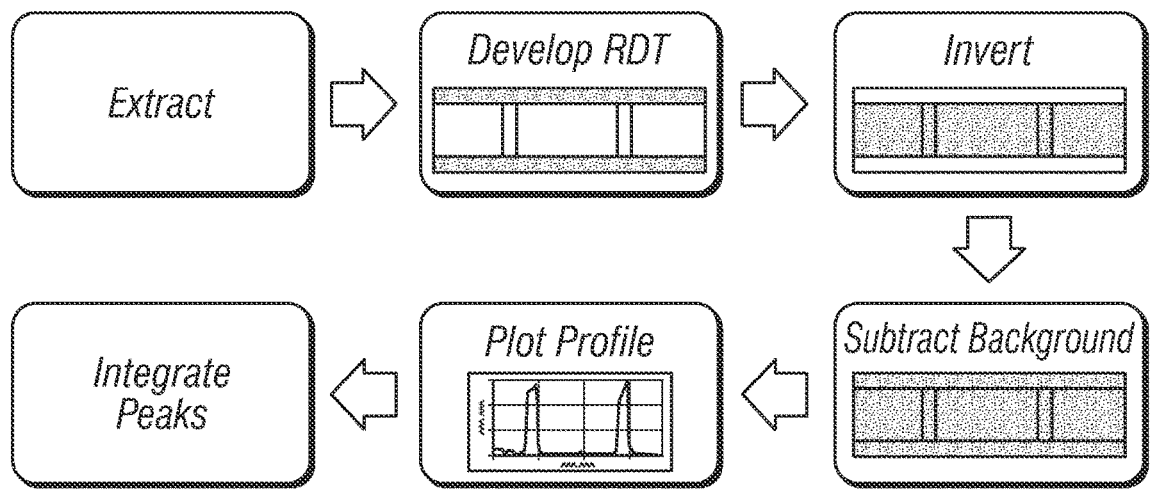
FIG. 7—Schematic of steps to quantitate the RDT signals.
Figure 8:
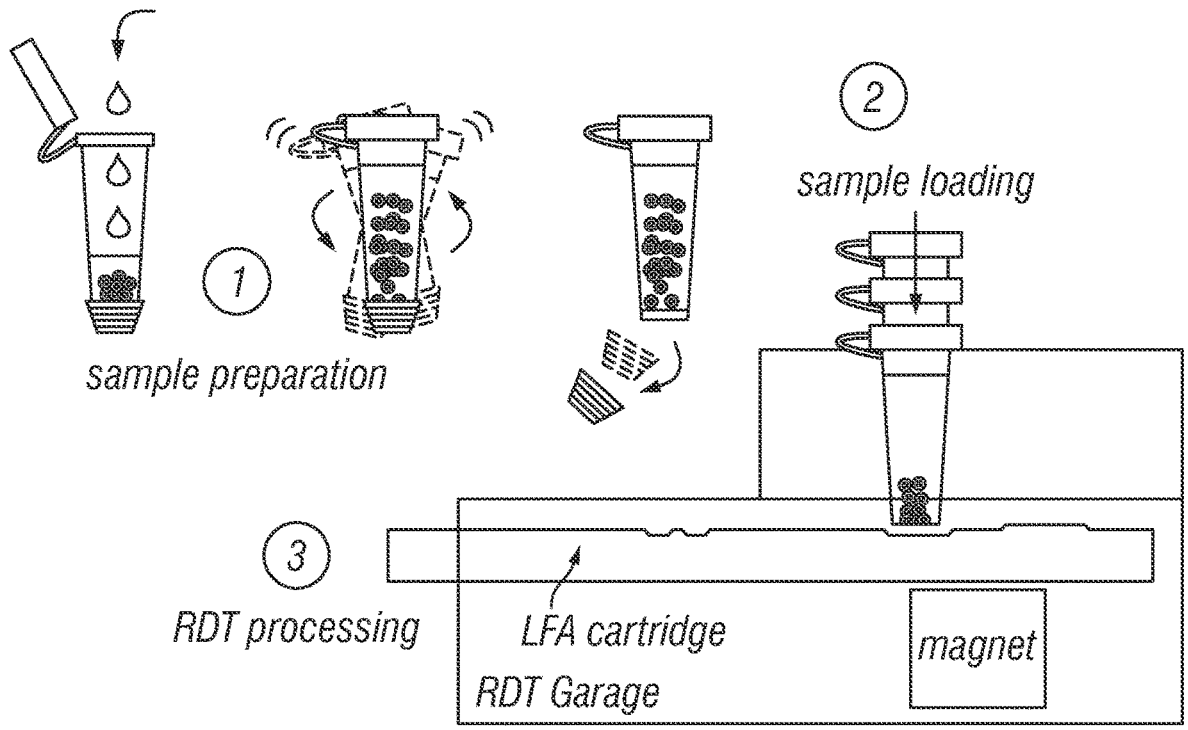
FIG. 8—mBEADS RDT garage. Workflow for the RDT Garage: (1) add and mix sample with magnetic beads to bind the biomarkers, (2) remove cap (surface tension retains sample) and insert tube into RDT Garage above the magnet to transfer biomarker-bound beads to the test, and (3) add buffer to develop the test.

An exemplary RDT garage device and a generalized workflow are illustrated in FIGS. 8 and 7, respectively. In general, the garage will have the following features:
 (a) a housing with a plurality of ports for receiving various device components;
 (b) a first port connected to a first internal chamber for reversibly receiving the rapid diagnostic test module;
 (c) a second port connected to a second internal chamber for receiving a sample, where the first and second internal chambers are connected by a passage that permits the sample to enter the first chamber; and
 (d) a third port connected to a third internal chamber for receiving a buffer, where the first and third internal chambers are connected to allow passage of the buffer into the first chamber.

The garage will be reusable and thus should be made of a durable substance such as a plastic/polymer that is sturdy but lightweight and can tolerate harsh conditions of heat and exposure. The material should be non-magnetic (ferromagnetic, paramagnetic, or superparamagnetic) so as not to interfere with the application of the magnetic field. Also, a somewhat rigid material is necessary to maintain form, so rigid or semi-rigid plastics are probably the most feasible materials. In particular, the use of a 3D-printable plastic would be highly desirable for locations where a 3D printer is accessible.

1. Sample Container

In one aspect, the RDT garage is designed to receive a sample container. The Sample container will house, prior to insertion into the garage, a sample and magnetic particles that contain a binding agent for a putative target that may be present in the sample. It may or may not contain an additional fluid for use in diluting or stabilizing the sample. In a particular embodiment, the container is a tube, with an attached or unattached cap for safely containing the contents of the tube. The materials for the sample container, like that of the garage, should be lightweight, durable, inexpensive and non-magnetic so as to not interfere with transit of the magnetic particles out of the container when the magnetic field is applied.

In a particular embodiment using the tube, the tube will also have a removable portion, the removal of which will create an opening that will allow the sample and magnetic particles to pass therethrough when subjected to a properly positioned magnetic field. The tube may contain scoring at the function of the removable portion such that manual pressure on the tube alone is effective to remove the removable portion. Alternatively, a separate device that is external to or internal to the garage may be utilized to remove the removable portion. It is, however, important that after removal, but prior to insertion into the garage, the contents of the tube do not passively exit from the tube.

In other embodiments, the tube may contain a small aperture that is insufficient in size to permit the sample to pass without some external force applied, e.g., a magnetic field, compression of the tube, negative pressure outside the tube. Alternatively, the garage itself may contain an element that will result in perforation of the tube upon insertion, permitting the sample to escape.

2. Chambers

Figure 9A:
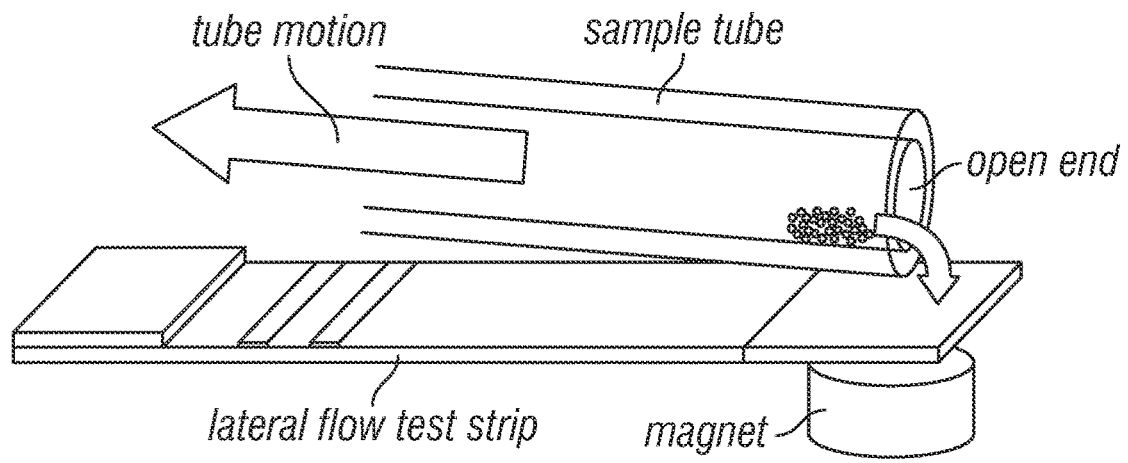
FIGS. 9A-C—mBEADS tube design. The tube design delivers magnetic beads with little or no sample volume to LFA.
Figure 9B:
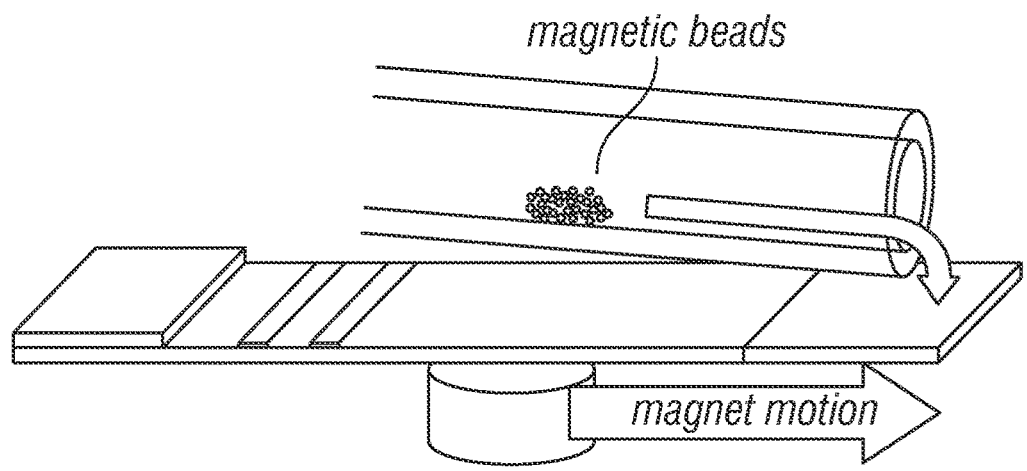
Figure 9C:
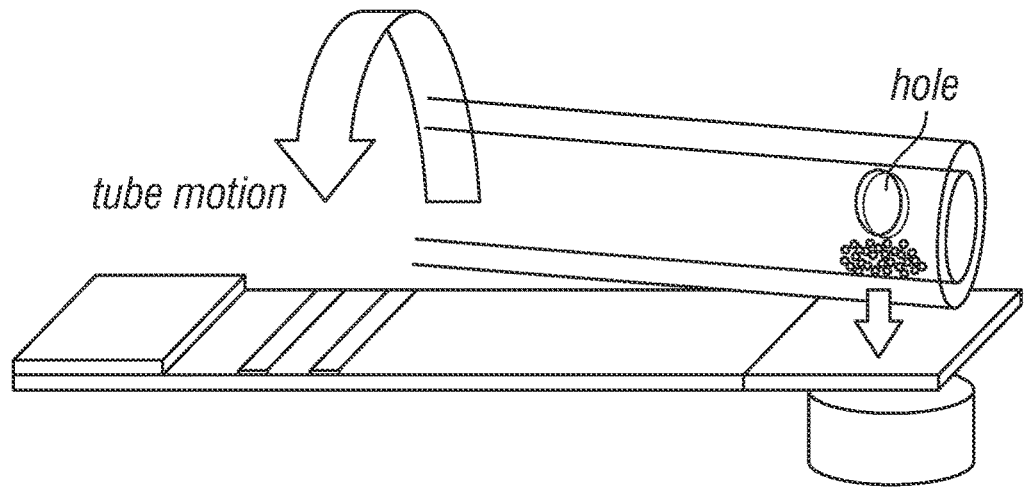
Figure 10:
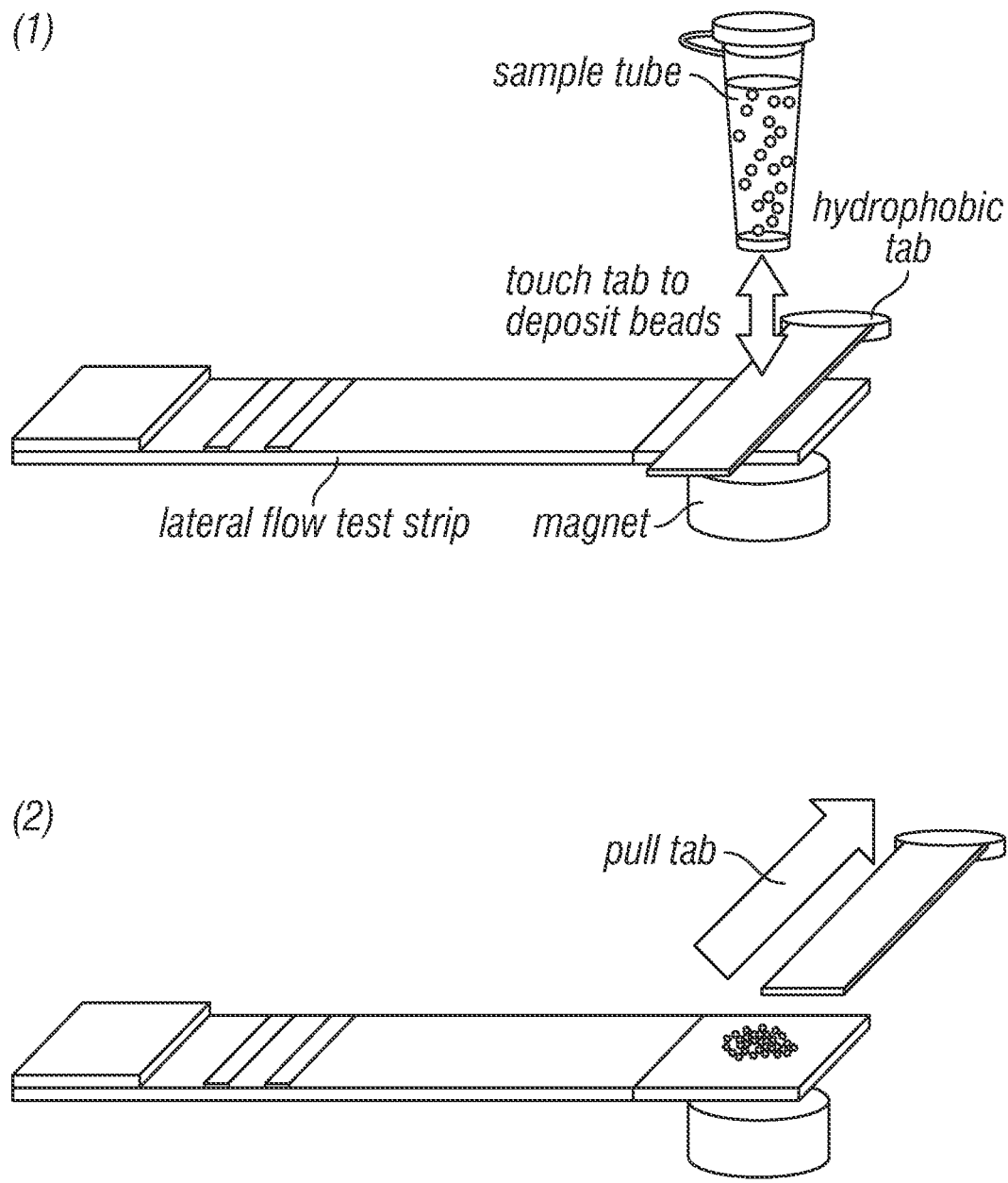

The RDT garage is designed to contain chambers that receive (a) the RDT cassette, the sample container, and the buffer. Examples of the disposition of the chambers and their relationship to one another are illustrated in FIGS. 7, 9 and 10.

RDT Chamber.

The RDT chamber will be positioned in the garage for simple insertion and removal of the test cassette. As shown in FIGS. 7, 9 and 10, the test cassette is inserted into an elongate, horizontal chamber that leaves openings in the test cassette facing upward and in operable connection with the Sample Container chamber and the Buffer chamber. The RDT Container chamber may optionally contain a feature that engages and corresponding element on the RDT cassette to lock the sample container into place.

Sample Container Chamber.

The Sample Container chamber is designed to receive the sample container and hold it in a position such that a magnetic field may be applied causing the magnetic particles to exit in the direction of the RDT cassette. As such, it must be in fluid connection with the RDT chamber. In the particular embodiment illustrated in FIGS. 7, 9 and 10 the Sample Container chamber is slightly smaller in diameter that a top flange of the tub such that the user will know when the sample container is fully engaged. The Sample Container chamber may optionally contain a feature that engages and corresponding element on the sample container to lock the sample container into place. The Sample Container chamber may also be configured such that when the sample container is fully engaged, the RDT becomes locked into place.

Buffer Chamber.

The Buffer chamber, as shown if FIGS. 7, 9 and 10, is arranged to receive the shaft of a pipette. However, this chamber may be designed in a variety of ways to receive the buffer from a wide source of buffer delivery systems including the aforementioned pipette, tubing, or other transfer device. It is advantageous, though not required, that the terminal portion of the delivery device be able to contact the surface of the RDT cassette, or at least to directly delivery the fluid to the RDT cassette with any substantial distance over which the buffer needs to move after exiting the delivery device.

Magnet Chamber.

In one version of the garage, the garage may contain a chamber or cavity for receiving a magnetic. While the magnet used may also be external to the garage, it may prove more convenient and reliable to have a more or less permanently located or fixed position magnet located within the garage such that upon introduction of the sample container into the garage, the magnet will be able to extract the magnetic beads from the sample container without any further manipulation.

3. Buffer and Delivery System

Another element of the system and methods described herein is a buffer delivery system. The buffer itself serves two primary functions as it relates to the RDT cassette: (1) it passively transports antigen and reactants down the RDT cassette via capillary (wicking) action; and (2) it optionally includes a substance that elutes the antigen from the magnetic particles. In one example, the inventors used a high concentration of imidazole to release the pfHRP-II malaria protein from the particles via competition for the reactants on the surface of the particles. However, other elution approaches could be used including altered pH or ionic strength, or competitive binding materials such as aptamers or peptides.

The delivery system, as already alluded to above, is very flexible in nature and may involve glass or plastic pipettes (standard or designed specifically for us in the garage), or tubing.

4. Particles

The particles for use in the present disclosure combine the functionalities of preferential binding to a class of molecules or to a select target of interest, susceptible to transport by magnetic force, and small size to increase reaction efficiencies and mobility.

The particles are magnetic or paramagnetic for embodiments subject to the application of magnetic fields. Commercially available magnetic or paramagnetic particles include Dynal beads (Invitrogen), which are 1 μm diameter, polystyrene matrix infused with superparamagnetic magnetite, and NiNTA Magnetic Agarose (Qiagen), which are 20 μm to 70 μm in diameter made of agarose matrix infused with paramagnetic magnetite. Useful particles sizes are about 1 μm to about 10 μm, with sizes including 1, 2, 3, 4, 5, 6, 7, 8, 9 and 10 μm and all ranges resulting from combinations thereof. Other commercial sources of magnetic particles include Promega, Spherotech, Polysciences, Ademtech, and Bangs Labs. Another consideration here is that a secondary magnetic particle could possibly be included in the mixture with the sole purpose of facilitating transfer across the air gap—a so-called "carrier particle."

Particles are derivatized to include on their surface binding agents that are capable of interacting with targets discussed below. These "reactants" are disposed on the surface of particles, where the targets can access them and interact. By reactant, it is not necessary that the material interact in any particular type of way. Rather, any physical interaction that permits association of reactant with the target cell is envisioned, such as covalent, non-covalent, electrostatic, hydrostatic, or ionic. For example, by coating a particle with an antibody, one can absorb cells expressing the antigen for the antibody to the particle to the exclusion of other biomolecules. Molecules that coordinate metals, in particular heavy metals, are also envisioned as reactants. Nickel and cobalt are in particular contemplated. One can also use non-specific binding to pull out a more general class of compounds based simply on their relative interaction with the reactants. Also, any natural or synthetic ligand that acts as a binding partner for a target will find use as a reactant.

To transfer biomarkers from patient samples to an LFA deposition pad, biomarkers may be captured on the beads surface in the patient sample and released onto the LFA using chemistries referred to in the literature as "catch and release" or "capture and release" chemistries. "Catch and release" chemistries are chemical agents that generally contain chemical linkers that are covalently or electrostatically attached to the bead surface on one end, with weaker bonds on the other end that are designed to capture the biomarker.

The capture end of the "catch and release" chemicals can be associated with the biomarker (in the case of direct catch and release) or associated with a secondary molecule that binds the biomarker (in the case of ligand-mediated catch and release). In each case, by design, the weaker bond can be selectively disassociated using release agents, such as small molecules, light, heat or pH, to release the biomarker or secondary molecule bound to the biomarker. An overview of several catch and release chemistries described in the literature are described in FIG. 14.

D. TARGETS

Targets will be found in fluids from non-human animals and humans. One of the powerful applications of the present technology is for use in low resource environments. Patient samples containing targets include blood, serum, plasma, sputum, urine, semen mucous or tears. Environmental samples may include lakes, streams, oceans, wastewater, industrial byproducts, etc.

The reactants can be any of a wide variety of biomolecules including proteins or nucleic acid aptamers. Other reactants include amino acids and small organic molecules. For two nucleic acids, the binding interaction will generally be characterized by hybridization, achieved by homologous base pairing. For one or more protein molecules, the interaction will generally be the formation of protein-ligand complexes which are reliant on the complementary structure and charge of the component molecules, such as antibody-antigen interactions and receptor-ligand interactions. Various types of molecules suitable for use in accordance with the present disclosure are described below.

Nucleic acids, proteins, small molecules, and other targets may be detected as described below as a means of detecting an isolated whole cell. They may also be detected apart from a whole cell as a second analyte for multiplex detection.

1. Nucleic Acids

The term "nucleic acid" is well known in the art. A "nucleic acid" as used herein will generally refer to a molecule of DNA, RNA or a derivative or analog thereof, including synthetic molecules. Nucleic acids are also defined as molecules containing a series of naturally-occurring purine or pyrimidine bases. The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to both single-stranded and double-stranded molecules, the latter being substantially or fully complementary to each other. A nucleic acid may even encompass a triple-stranded molecule. As used herein, a single stranded nucleic acid may be denoted by the prefix "ss," a double-stranded nucleic acid by the prefix "ds," and a triple stranded nucleic acid by the prefix "ts."

DNAs are defined as nucleic acids containing adenine "A," guanine "G," thymine "T" and cytosine "C." DNA molecules, both single- and double-stranded, may be utilized in accordance with the present disclosure. DNAs may comprise coding sequences or non-coding sequence, and genomic sequences or cDNAs, synthesized strands homologous to the target of interest. DNA "arrays"—collections of DNAs that represent a group of selected probes.

RNAs are defined as nucleic acids containing A, G, uracil "U" or C. Both single- and double-stranded RNAs, may be utilized in accordance with the present disclosure. Because of their labile nature, additional steps must be taken to preserve the integrity of RNA containing samples. In particular, the ubiquitous presence of RNAses requires the use of RNAse inhibitors such as DEPC.

2. Proteins

In another embodiment, the probe may be a proteinaceous compound. There are wide varieties of protein-protein interactions; however, proteins also bind nucleic acids, metals and other non-proteinaceous compounds (e.g., lipids, hormones, transmitters). Some examples of protein that may be used as either targets or probes are listed below.

(a) Antibodies

Antibodies may be used as probes for unknown molecules, or they maybe the target for reaction with a known probe. The antibodies may be either polyclonal or monoclonal in origin. Methods for preparing antibodies are well known to those of skill in the art and need not be discussed here. Antibodies may be fixed to the filament support using standard techniques.

Obviously, identifying antibodies that bind to certain target molecules is an important goal that could be accomplished by the present disclosure. However, the present disclosure also permits the screening of samples for the presence of antibodies. For example, a particle might contain a variety of bacterial and viral antigens, which could assist in diagnosis of infectious disease by identifying relevant antibodies in an affected subject.

(b) Enzymes

Enzymes are proteins that facilitate the modification of a wide variety of compounds including nucleic acids, other proteins, lipids, sugars, steroids and many other compounds. Particular types of assays contemplated include identifying inhibitors of enzymes that bind to, but are not processed by, the enzyme. Alternatively, identifying compounds that are bound by an enzyme may assist in design of pro-drugs that are processed by an enzyme.

(c) Receptors

Receptors are molecules that facilitate signaling processes by binding their cognate ligand moieties. Once bound, the receptor will then perform some other function (enzymatic, intracellular translocation, cell permeability) that effects the signaling. Identifying molecules that block receptor function, or mimic the natural ligand, can be accomplished using the present disclosure.

(d) DNA-Binding Proteins

Another important class of proteins is the DNA binding proteins. These proteins include polymerases, helicases, ligases, and transcription factors. The proteins have varying degrees of DNA sequence specificity can be assessed for ability to bind varying DNA sequences. Conversely, providing a DNA sequence as a probe, once can identify unknown binding proteins with specificity for that sequence.

3. Small Molecules and Other Targets

A wide variety of "small molecules" can be examined for their ability to interact to a given reactant. These libraries comprise non-protein and non-nucleic acid molecules. Alternatively, libraries can be constructed around particular "pharmacores" that are believed to provide basic structural features necessary for a particular drug to function.

Also, compounds such as liquids, carbohydrates, metals, drugs (both legal pharmaceuticals and illegal drugs) and toxins may be assayed using the devices and methods of the present disclosure.

4. Labels

In various embodiments, it may desirable to label particles, reactant, or target molecules, including molecules that are used as positive or negative controls. Examples of labels include paramagnetic ions, radioactive isotopes, chemiluminescent compounds, fluorophores, chromophores, NMR-detectable substances, and X-ray imaging compounds.

Paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

Radioactive isotopes include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often preferred for use in certain embodiments, and technicium$^{99m}$ and/or indium$^{111}$ are also often preferred due to their low energy and suitability for long range detection.

Among the fluorescent labels contemplated for use include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Enzymes (an enzyme tag) that will generate a colored product upon contact with a chromogenic substrate may also be used. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

E. mBEADS EMBODIMENTS

As discussed above, mBEADS (magnetically-enabled biomarker extraction and delivery system) is an ideal system to apply to sample processing in low resource environments. The system incorporates a magnetic beads that are surface-derivatized to contain reactants that bind target molecules in various samples. The system permits for rapid, low cost and simple pre-processing of the samples, thereby permitting the applications of assays in low resource, point of care environments.

1. Tube Delivery

In the tube delivery embodiment, a tube containing the patient sample and the biomarker-bound beads is positioned above the LFA and aligned with a magnetic field to pull the beads out of the open end of the tube or out of a hole in the wall of the tube (see FIG. 9). The sample is retained in the tube by surface tension as the other end is sealed. The beads inside of the tube are transferred to the LFA by (1) sliding the tube away from the LFA and magnet until the beads drop out the end of the tube, (2) sliding the magnet below the LFA along the axis of the tube until the beads drop out the end of the tube, and (3) rotating the tube above the LFA and magnet until the bead drop out the hole in the side of the tube.

2. Hydrophobic Pull Tab

This embodiment adds a barrier between the end of the sample tube and the LFA to control the dispensing of the magnetic beads (see FIG. 10). In the presence of a magnetic field, the magnetic beads are transferred onto the barrier, in this case a hydrophobic material, by touching the open end of the tube containing the magnetic beads to the hydrophobic material. Touching the open end of the tube disrupts the surface tension interface that retains the beads, reducing the force required for the beads to leave the tube. Minimal liquid is transferred because the hydrophobic nature of the barrier will not adhere to the aqueous liquid and the bulk of the liquid phase is drawn back up into the end of the tube. Importantly, the magnetic beads are retained on the surface by the magnet beneath the LFA & hydrophobic surface. Beads are then applied to the LFA surface by pulling the tab laterally out from under the beads. Beads slide along the surface of the beads because the magnetic field strength pulling them toward the LFA overcomes the friction forces pulling them laterally with the hydrophobic tab in a manner similar to the classic demonstration of pulling a table cloth out from under dishes on a table.

3. Sheath Design

Figure 11:
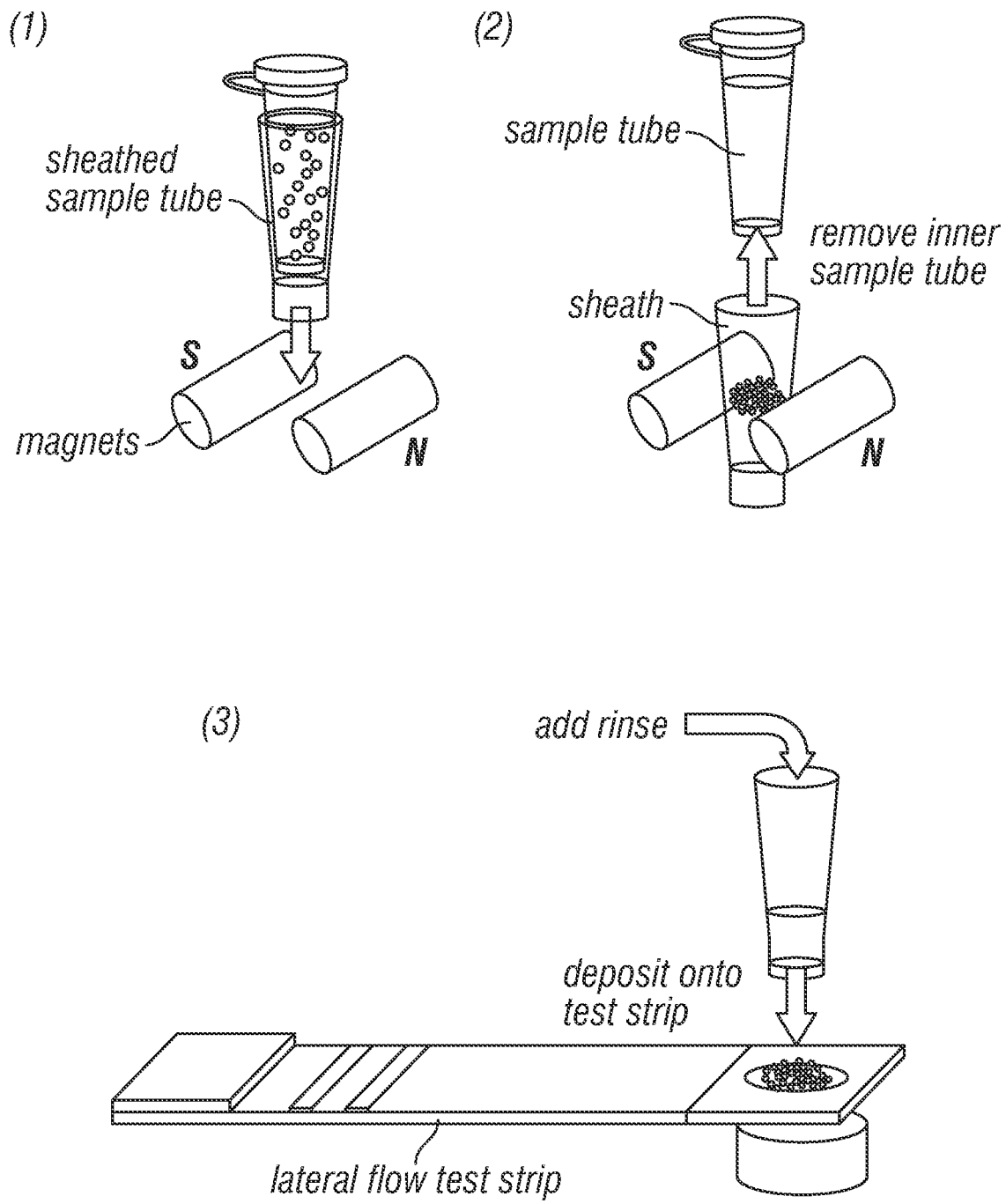
FIG. 11—mBEADS sheath design. Transfer of magnetic beads with captured biomarker across an air-liquid surface tension valve. (1) Insert sheathed sample tube between magnets. Magnets retain magnetic beads. Opposed magnets shown but could also be done with single magnet. (2) Remove inner samples tube to transfer beads to wall of outer sheath tube. One can rotate the inner tube to mix beads with sample more thoroughly. (3) Add rinse solution to resuspend beads. Rinse solution is anticipated to be a smaller volume than initial sample. Rinse solution could already present in outer tube. Spotting onto the test strip will transfer beads and some solution. Magnet underneath could be used also but used to transfer beads & likely less fluid. Need to move magnets away from tube after second step so that beads are not permanently stuck on wall.

This embodiment adds a secondary container or sheath that slides over the end of the sample tube to control the dispensing of the magnetic beads onto the LFA (see FIG. 11). The beads are transferred to the sheath by removing the inner sample tube from the sheath in the presence of a magnetic field. As the inner sample tube is withdrawn the magnetic beads are pulled to the bottom of the sample tube and out through the surface tension valve at the bottom of the tube. As in the othe examples, the basic idea is to retain the bulk of the sample liquid and transfer only a small volume with magnetic beads as they move out of the sample volume. The advantage of this approach is that the sheath containing the beads can be used as a secondary container that can be used to rinse or further process the beads prior to adding them to the LFA. In principle and number of consecutive concentric sheaths could be used to perform multiple processing steps.

4. Pre-Release Design

Figure 12:
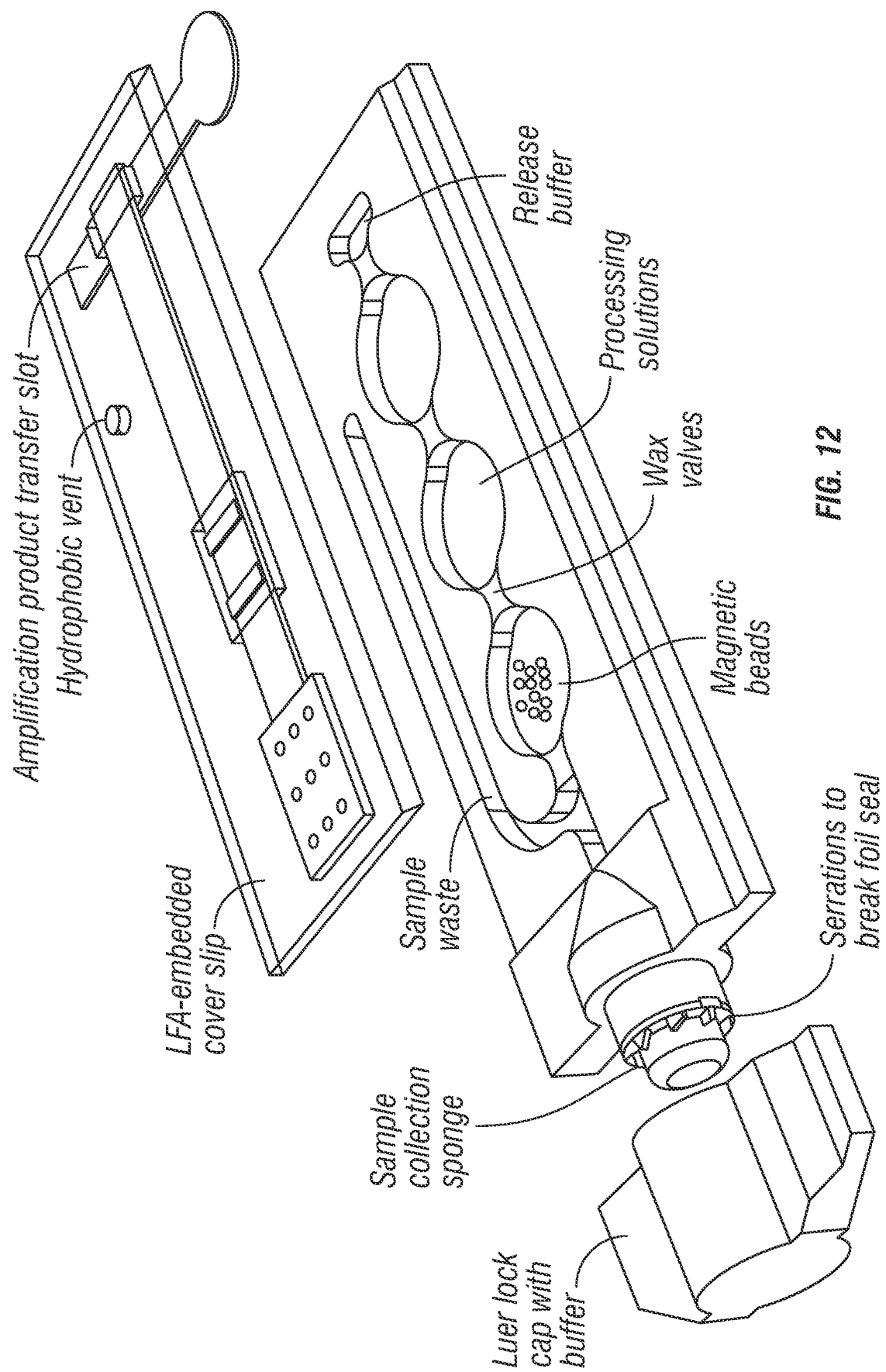
FIG. 12—mBEADs pre-release design. In this design there can be multiple processing steps. Biomarkers are released into a processing solution prior to being applied to the LFA test strip. A hydrophobic pull tab is shown to separate the release buffer from the LFA test strip until the biomarkers have been released.
Figure 13A:
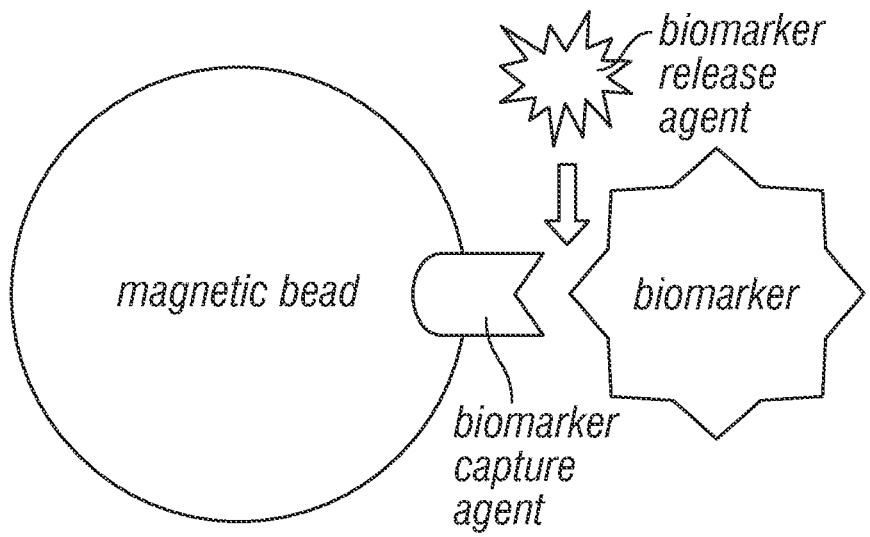
FIGS. 13A-B—Catch and Release Chemistries using mBEADS. Two general mechanisms for biomarker catch and release from the surface of magnetic beads.
Figure 13B:
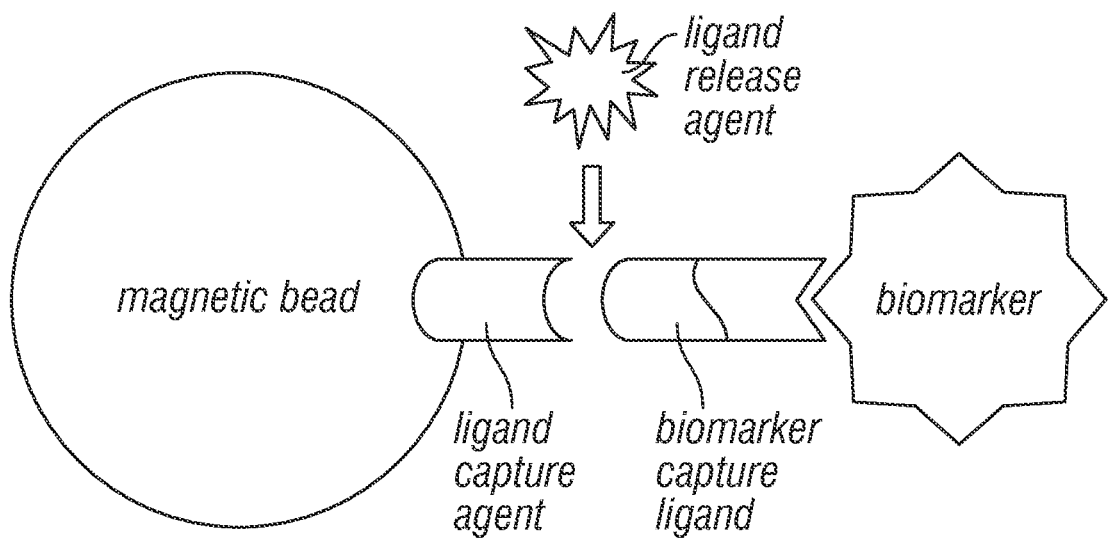

This embodiment includes (an) additional processing container(s) after the initial mixing/binding container to further process the beads (see FIG. 12). In this design, the biomarkers can be released from the beads. The key feature that differentiates this embodiment from the others is the use of a pull tab to separate the LFA and a chamber containing biomarkers released from the beads into a final elution chamber. Processing is carried out by passing through successive chambers until release in a final chamber containing a contact area sealed by the pull tab. On the other side of the tab surface is the surface of the lateral flow strip. When the tab is removed fluid will transfer by capillary action directly onto the surface of the lateral flow strip and begin to move up the strip by capillary action.

F. MAGNET PROCESSING OPTIONS

Most of the previous work by the inventors has relied on a single magnet to trap magnetic beads in a solution in a small volume against the side of a container. However, the use of multiple magnetics can create shaped magnetic field gradients within a solution. These fields result in more controlled manipulation of bead positions and a reduction in the compaction of the bead mass against a container wall. The result is a more controlled transport within the solution, better interaction of the bead surface with the solution contents, and better movement of the beads across surface tension interfaces.

An examination of the external magnetic fields and the position of magnetic beads within a tube illustrate some of the differences among two designs (single magnet to the side of a tube, and two separate magnets in an attractive opposed magnet design). In all of these designs, an external magnet is moved to the right along a tube to position magnetic beads contained within the tube within sequential reaction solutions. The effects of these magnetic field designs are illustrated. The equilibrium position, that is the balance between fluid viscosity & moving magnetic field effects, is quite different. In the case of the single magnet on the side of the tube, the position of beads trails the magnet and is found at point where the field lines are most concentrated. In the case of two opposed magnets, the position of the beads is quite different. With this configuration, the beads remain collected within the tube in a more central disposition and are not packed against the tube wall. This less compact bead distribution is critical to achieving maximum interaction between the fluid phase and the surface of the beads.

The inventors' current interpretation of why these differences exist is that as the magnetic field moves along the tube the beads are collected and collected in regions of the magnetic field where the magnetic gradients are the steepest. In the current design, the steepest gradients within the tube are opposite the corner of the magnet. Furthermore, at this point within the tube the direction of the magnetic gradient is towards the magnet pole, hence the beads collect at the wall of the tubing. On the other hand, in the two magnetic design, the steepest gradients are in the center of the tube and in the direction along the tube axis.

Static magnetic fields are determined by the shape of the permanent magnet and the degree of magnetization, measured by the remnant (magnetic) flux density. Magnetic (and electric) fields can also be generated by an electric current in a wire, often in the shape of a coil though other shapes are possible and may even be desirable. The magnetic field and its gradient from a coil can be enhanced by the use of a ferrous metal to conduct and concentrate the magnetic field. Most of the single magnet designs that we have used create magnetic field gradients between $5 \times 10^{-4}$ Tesla/meter and $2.2 \times 10^{-3}$ Tesla/meter. In opposed two magnet designs, this magnetic field gradient ranges from 0 to $1.35 \times 10^{-3}$ Tesla/meter. The shapes of the these fields are quite different, and the inventors currently believe that this difference is important for producing the effects they observe relating to confinement of the beads within the filed during their motion within a tube. The other major determinants of the effects of the magnetic fields are the distance between the magnet and the magnetic beads (in general this falls off with the distance cubed), and the magnetic susceptibility of the beads themselves.

1. Single-Side Magnet

Figure 15A:
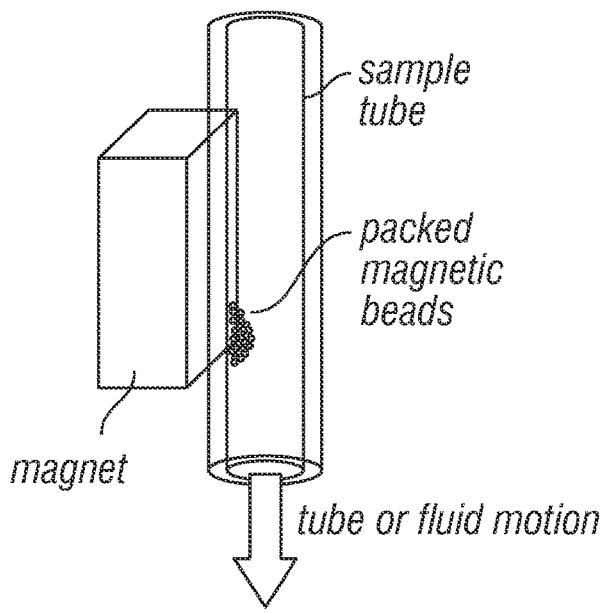
FIGS. 15A-E—Magnetic orientations used with mBEADS. Two types of magnetic orientations used in mBEADS.
Figure 15B:
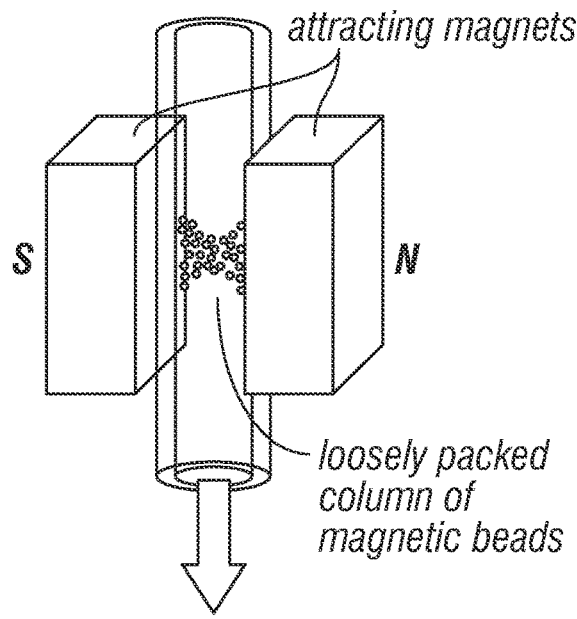
Figure 15C:
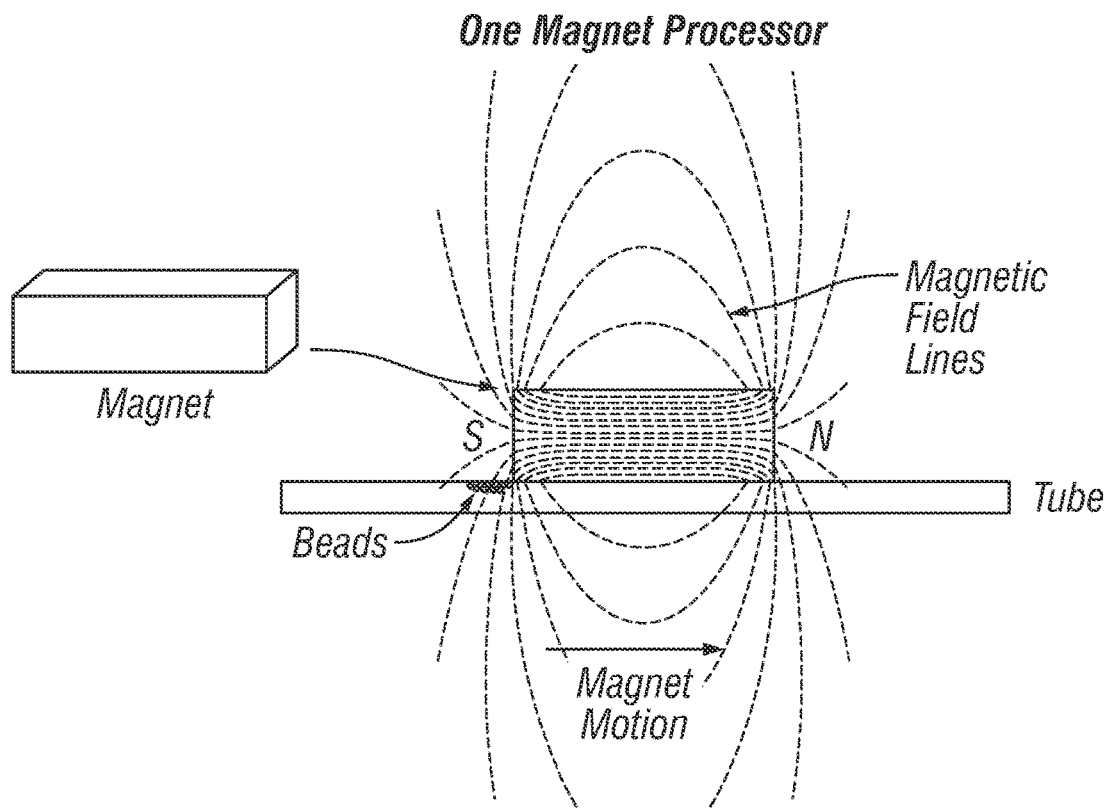

In this magnetic orientation, the magnetic beads are packed onto the inner wall of the tube (see FIG. 15A and FIG. 15C). This orientation works well for moving the magnetic beads down the tube or for retaining the magnetic beads while moving the fluids through the tube. This orientation does not work well for maximizing interactions with the surface of the magnetic beads and the fluid while mixing the magnetic beads with the sample.

2. Two Attracting Magnets

Figure 15D:
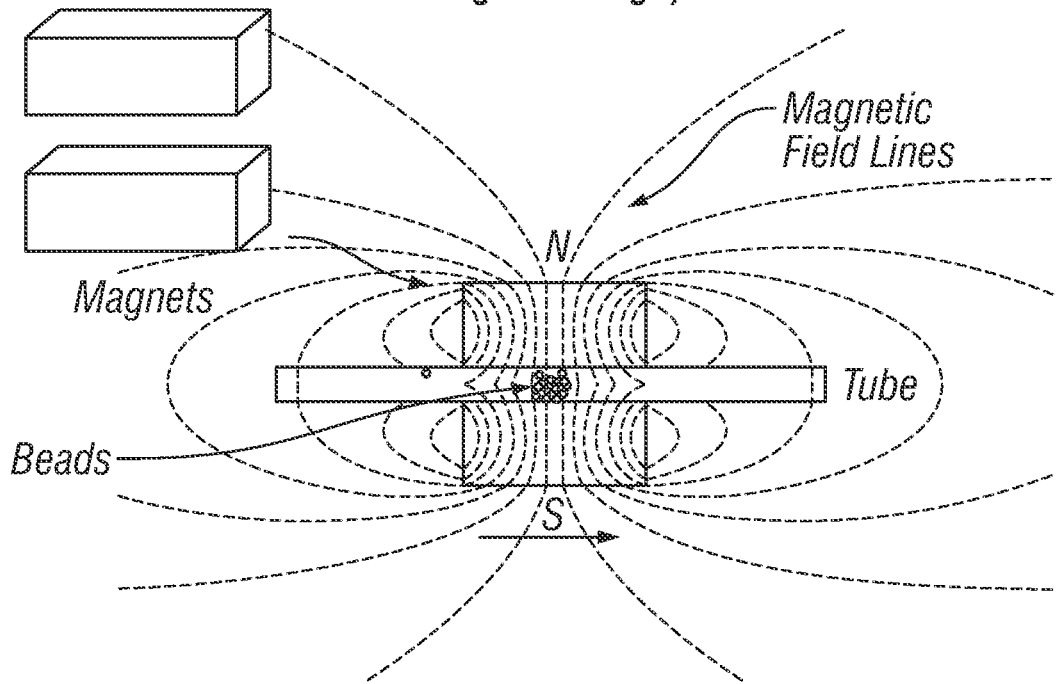
Figure 15E:
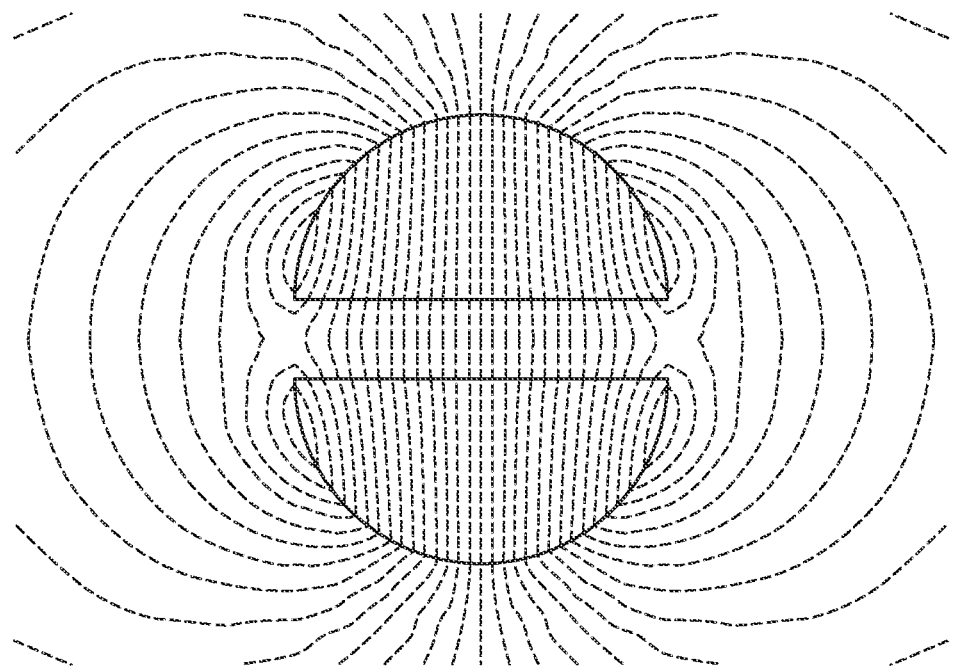

In this magnetic orientation, the magnetic beads are distributed in a loose column inside of the tube (see FIG. 15B and FIG. 15D) instead of a compact clump seen with the single magnet design. This orientation works well for moving the magnetic beads down the tube, for retaining the magnetic beads while moving the fluids through the tube, and for maximizing interactions with the surface of the magnetic beads and the fluid while mixing the magnetic beads with the sample. FIG. 15E illustrates what appears to be the optimal design that of two opposed hemi-spherical magnets.

3. Quadrupole Magnets

In this four magnetic orientation (two pairs of attracting magnets across a section of the tubing), the magnetic beads are distributed in a loose column inside of the tube instead of a compact clump seen with the single magnet design. This orientation works well for moving the magnetic beads down the tube, for retaining the magnetic beads while moving the fluids through the tube, and for maximizing interactions with the surface of the magnetic beads and the fluid while mixing the magnetic beads with the sample.

4. Field-Focused Magnets

Another alternative to the attracting magnets designs described above is the use of materials that conduct magnet fields. For example that placement of a ferromagnetic block of material opposite of the magnet will achieve similar field lines without the use of a second magnet.

5. Electromagnets

Another alternative is the use of electromagnets to shape the magnetic fields. The main advantage of electromagnetics is that the fields may be altered in time and this dynamic change can be sued to modify the filed lines over time and modify bead motion or mixing.

G. KITS

According to the present disclosure, there are provided kits containing reagents and devices described above. Generally, kits comprise separate vials or containers for the various reagents, such as particles, reactants, and detection reagents—either as liquids or as lyophilized solids. In the case of the latter, suitable solvent may be included, such as water, ethanol, various buffer solutions, and the like. The reagents may also be provided in one or more devices in a ready-to-use form, i.e., located in various devices, optionally with reactants included. The device, particles, reactants and/or reagents may be disposed in vials or containers held in blow-molded or injection-molded plastics. The kit may also contain instructions for performing the methods described herein.

H. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods

Methods. Both pooled and individual donor human whole blood in citrate phosphate dextrose (Cat # HMWBCPD) was purchased from Bioreclamation LLC. For the enhancement study pooled blood was used. For the individual donor effect study, individual donor blood was used as shown in Table 1. This study was blinded, as the inventors did not know the identity of the donors. *Plasmodium falciparum* D6 strain was cultured in the lab. Tygon tubing was purchased from McMaster Carr (Cat # ACF00002). Ni-NTA Magnetic Agarose Beads (Cat #36113) were purchased from Qiagen Inc. Donut magnet used in this study was purchased from Emovendo LCC. Paracheck (Pck), ParaHit Dipstick (PDip), ParaHit Total (Ptot), ICT Pf (Ipf), ICT Dual (Idual) and Blue Cross One Step Pf (OsPf) rapid diagnostic tests were acquired from their respective manufacturers. Hewlett Packard Color LaserJet CM3530fs MFP scanner was used to image the RDTs. Image J software was downloaded from the National Institute of Health website (http at //rsbweb.nih-.gov/ij/). OriginPro 9.0 Software was employed for RDT analysis. The remaining products were purchased from either Fisher Scientific or Sigma Aldrich.

Blood Sample Preparation.

Human whole blood samples were combined in 1:1 (v:v) ratio with 2× lysis buffer (100 mM potassium phosphate pH=8.0, 600 mM NaCl, 250 mM imidazole, 2% Triton X-100). Subsequently, the blood sample was filtered through glass wool that was placed in the bottom of a plastic syringe. Following filtration, a 200 parasite/μL stock blood sample was made by adding a specific amount of D6 *P. falciparum* culture (at ~52000 parasites/μL) to the lysed and filtered sample. The remaining parasitemias were achieved by serial dilution of the 200 parasites/μL stock. For the mimic patient study, this process was modified slightly in that the specific amount *P. falciparum* culture required for the desired parasitemia was spiked into the sample before filtration. Thus, the samples were prepared individually without dilution.

Extraction and Analysis with RDTs.

Extraction devices were constructed and prepared blood samples were purified and concentrated as described previously (Davis et al., 2012). Briefly, a 9-inch piece of Tygon tubing was injected with three 100 μL wash chambers (50 mM PB, pH 8.0, 300 mM NaCl, 125 mM imidazole, and 0.05% Tween 20) each separated by a 0.25 μL mineral oil valve. An elution chamber consisting of 10 μL of elution buffer (50 mM potassium phosphate (PB), pH 8.0, 300 mM NaCl, 500 mM imidazole, 0.05% Tween-20) was injected at the end of the tube. One end of the Tygon tube was blocked with a capillary tube and a PCR tube was placed on the other end as the sample chamber. 200 μL of the blood sample were placed into this chamber with 10 μL of NiNTA magnetic agarose beads. After incubation in the chamber, the beads were pulled through the wash chambers into the elution chamber with a magnet. After incubating in the elution chamber the beads were pulled back into the adjacent oil valve. The elution chamber was then cut off with a razor and the contents were spotted onto an RDT. In the enhancement study, this process was done, in triplicate, on six types of RDTs, at six parasitemias (0, 12.5, 25, 50, 100 and 200 parasites/μL). For the individual donor effect study, the process was done in triplicate for three parasitemias (0, 10 and 100 parasites/μL) with each donor sample on three RDT brands, Ptot, Ipf and Pck, of low to high performance, respectively, based on the WHO report. For both studies, analysis of the samples that were not extracted consisted of spotting 5 μL of the filtered and parasite spiked blood sample directly onto the RDT and processing according to manufacturer's specifications.

Image Analysis.

Figures 3, 4, 6:
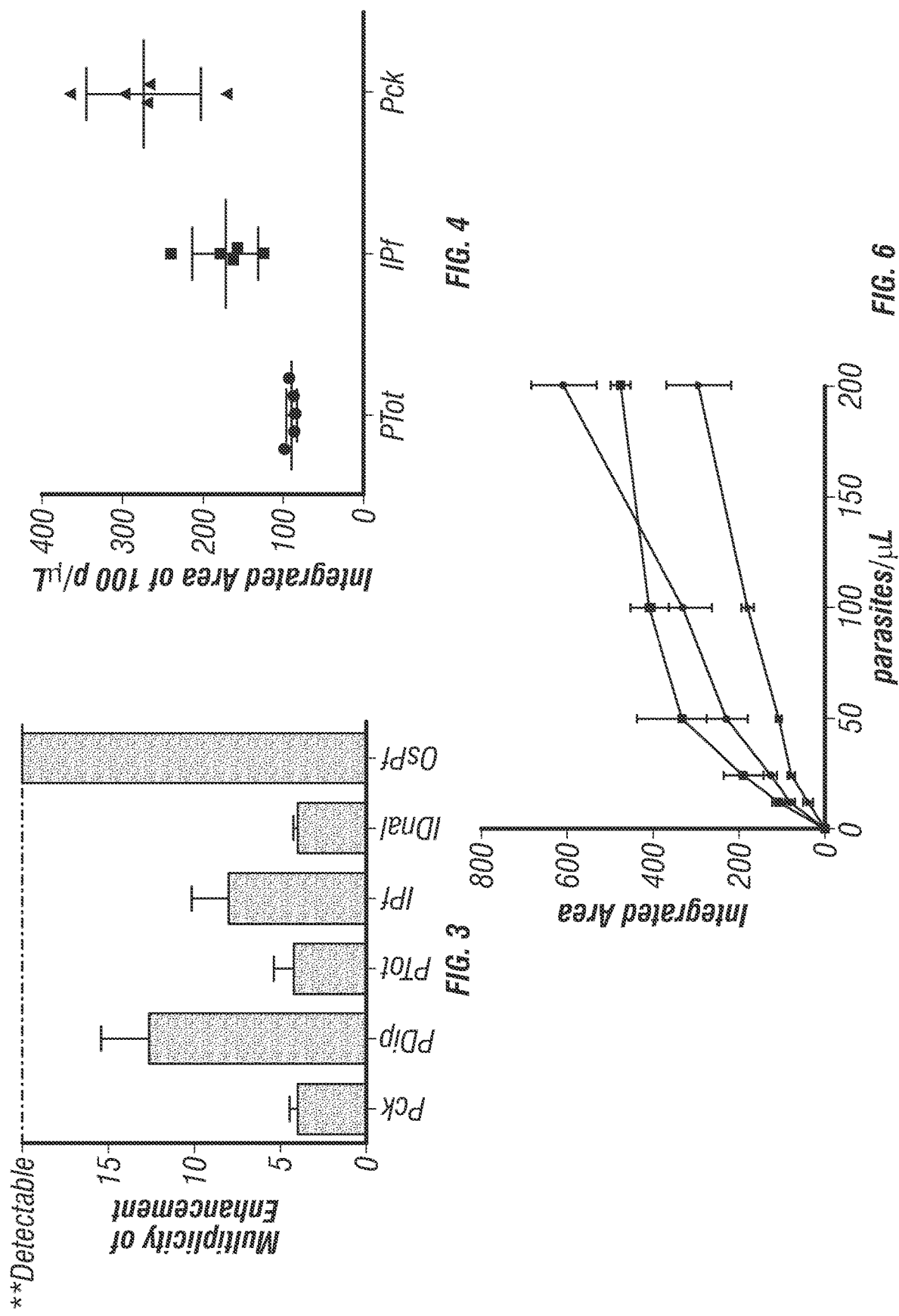
FIG. 3—The multiplicity of enhancement observed at 200 parasites/μL for each RDT brand, as a result of extraction.
FIG. 4—Quantitative performance of three RDT brands for five blood donor samples spiked with P. falciparum culture to a final concentration of 100 parasites/μL. PTot: Donor 1 (second from right), Donor 2 (second from left), Donor 3 (far right), Donor 4 (middle), Donor 5 (left). IPf: Donor 1 (top), Donor 2 (second from bottom), Donor 3 (bottom), Donor 4 (middle), Donor 5 (second from top). Pck: Donor 1 (second from top), Donor 2 (middle), Donor 3 (second from bottom), Donor 4 (top), Donor 5 (bottom). The WHO panel detection scores for Parahit Total (PTot), ICT Pf (IPf) and Paracheck (Pck) are 35.4%, 86.9% and 96.0%, respectively.
FIG. 6—Comparison of the titration curves for three of the RDT brands used for the study on the effect of individual donor samples, which show differences in brand performance. The WHO panel detection score for each brand tested is indicated on the graph.

The process used for analysis of the RDTs is outlined in FIG. 6. To begin the image analysis portion of this workflow the immunochromatographic test strip, housed within the plastic cassette of the RDT, was removed. The absorption pad at the end of the strip was detached to aid in the drying of the strip. The dry strip was then imaged with a Hewlett Packard Color LaserJet CM3530fs MFP scanner. Specific settings were used (darkness=8, background=1, sharpness=4) and the highest image quality was selected. The image was then manipulated in Image J. First, the image was inverted. This is a processing step commonly performed in RDT reader algorithms to present the data in an intuitive manner (Mudanyali et al., 2012). Secondly, the background was subtracted (rolling ball radius=15 pixels, smoothing disabled). Once this was accomplished, a plot profile containing the test and control line was generated. This profile was imported into Origin® software, where the peak in the plot profile associated with the test line was integrated using the Peak Analysis tool. When using this tool, the automatic background line was used. A test was considered positive if the height of the test line peak on the plot profile was at least 3% of the control peak. Peak width was determined manually by the user, and the result of the integration was generated by the software. This result was used to quantitate the intensity of the test line in the form of an integrated area.

Example 2—Results

Enhancement in RDT Performance.

Figure 2:
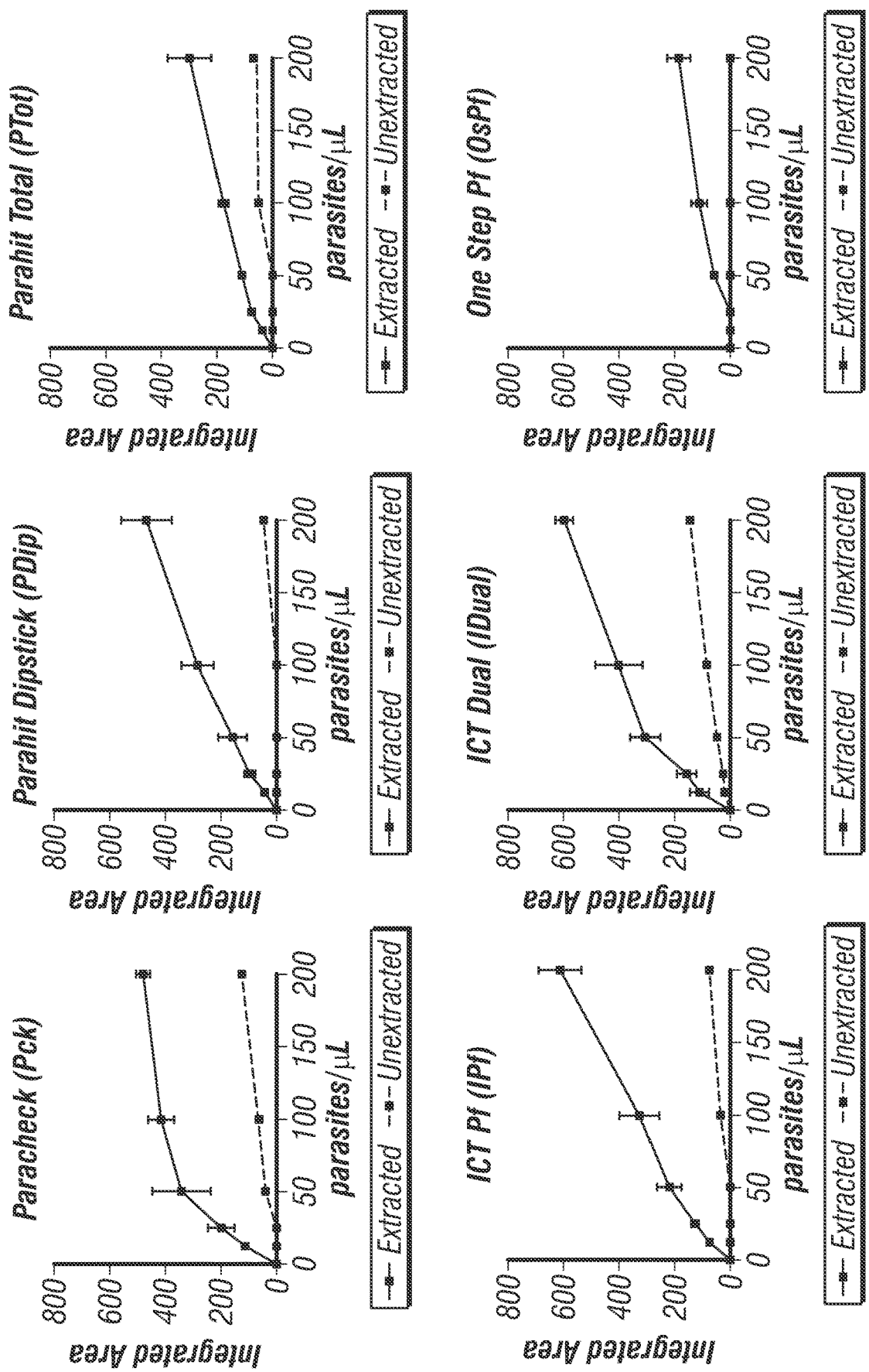
FIG. 2—Integrated area of the RDT signal as a function of parasitemia, extraction and RDT brand. Curves for extracted (black lines) and unextracted (dashed line) samples are shown and the signal increase gained from extraction can be seen.

The effect of sample preprocessing on RDT performance can be seen in FIG. 2. This analysis showed five of the six RDT brands tested were able to detect 200 parasites/µL from an unextracted sample. Four brands detected 100 parasites/µL, as compared to only two at 50 parasites/µL. Only Idual detected unextracted samples at 25 and 12.5 parasites/µL. After extraction, all brands were improved to detect parasites at concentrations of 12.5 parasites/µL, and higher, with the exception of OsPf. However, as is shown in FIG. 2, the control line was missing on random tests from one lot (Lot #10006) of Ipf RDTs. Upon switching to a new lot, this issue was resolved.

To quantitate performance, the lateral flow strips within each cassette for all brands were scanned and the corresponding plot profiles analyzed using peak integration software. Analysis methods of this type are common in recently developed RDT readers (Mudanyali et al., 2012). The degree of enhancement in RDT signal that occurs with extraction of the sample (enhancement factor) was calculated for 200 parasites/µL by the following relationship:

$$\text{Integrated Area}_{extracted}/\text{Integrated Area}_{unextracted}$$

(FIG. 3). This enhancement factor ranged from 4 to 13 among the five brands that produced a detectable signal at 200 parasites/µL unextracted. For OsPf, the enhancement was practically infinite, as the unextracted sample was not detected at 200 parasites/µL (FIG. 3).

Limit of Detection of Enhanced RDT Signal.

Figure 5:
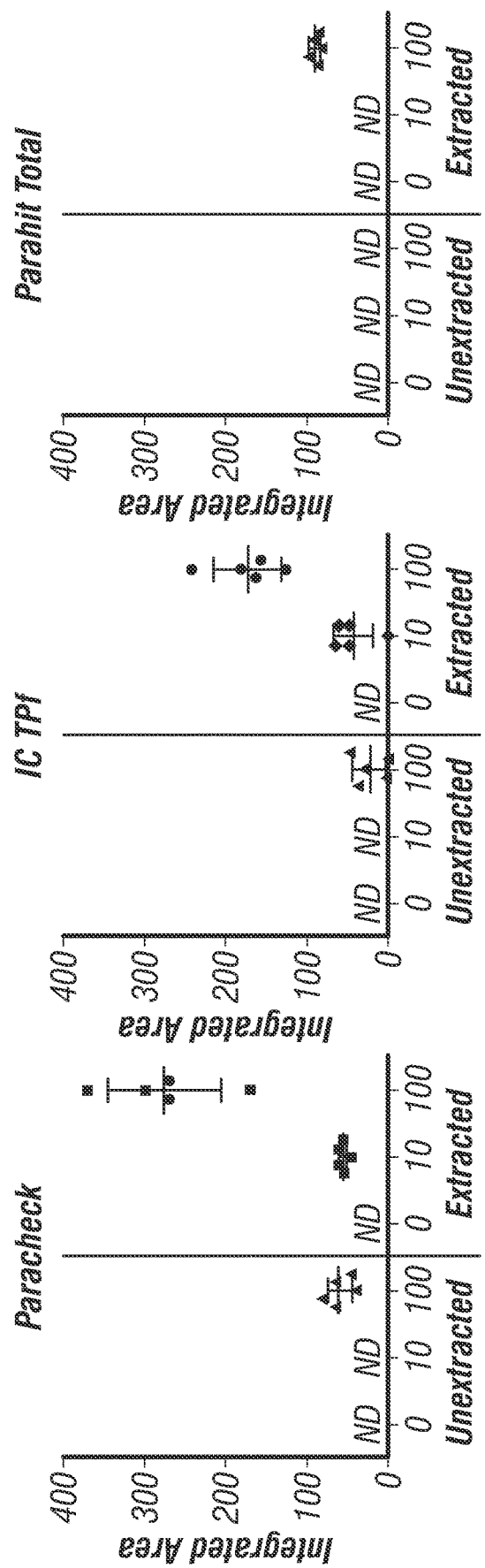
FIG. 5—Plots of the average peak areas from the RDT test lines for each surrogate patient sample, extracted and unextracted, at all parasitemias.

Given the nature of the algorithm used to detect the peaks on the scanned RDT image, the smallest detectable signal was found as a percentage of the control peak (threshold height). For each brand tested, the integrated area for all of the control lines analyzed were averaged and converted to the 3% threshold height maximum. Given this threshold height, the LOD was found for extracted and unextracted samples of each brand (FIG. 4). Both Pck and Idual had LODs of 3 parasites/µL after extraction (Table 1). Additionally, a sensitivity enhancement factor was calculated by taking the ratio between the LODs for RDTs run with unextracted and extracted samples. This value ranged from a 4-fold to 13-fold enhancement in sensitivity. The sensitivity enhancement factor could not be calculated for OsPf because this brand did not flag within the parasitemias tested (FIG. 5).

TABLE 1

Limit of Detection (in parasite/µL) for All Brands of RDTs Tested with Unextracted and Extracted Samples

| Brands | Unextracted | Extracted |
| --- | --- | --- |
| Paracheck (Pck) | 21.7 ± 7.4 | 3 ± 0.2 |
| Parahit Dipstick (Pdip) | 143.7 ± 39.5 | 10.7 ± 0.9 |
| Parahit Total (Ptot) | 70.2 ± 12.4 | 17.3 ± 1.5 |
| ICT Pf (Ipf) | 51.1 ± 7.9 | 5.6 ± 0.8 |
| ICT Dual (Idual) | 15 ± 1 | 2.9 ± 0.2 |
| One Step Pf (OsPf) | ND | 32.6 ± 4.5 |

Effect of Individual Donor Samples on RDT Performance.

To focus the study on the correlation between donor source and WHO panel detection score (PDS) and the RDT signal intensity, three RDT brands of low, medium and high performance were selected. The performance of each RDT brand is based on the WHO PDS which is established by the RDT brand's inter-test and inter-lot consistency (World Health Organization, 2011). The three brands were selected by their WHO PDS and Pck fell in the high (>90%), Ipf in the medium (50-90%) and Ptot in the low (10-40%) range. These three brands were tested with unextracted and extracted samples at 0, 10 and 100 parasites/µL, to demonstrate their utility at low parasitemias. As can be observed in FIG. 4, the extracted donor samples at 100 parasites/µL had average signal intensities that were statistically different among brands and trended with their respective PDS.

The highest signal intensities for the extracted samples were observed for Pck, which had a PDS of 96.0%. Signal intensity decreased for Ipf followed by Ptot, whose detection scores were 86.9% and 35.4%, respectively. In FIG. 5 it can be seen that when unextracted donor samples were applied to Pck, 5/5 were detected at 100 parasites/µL, while 0/5 were detected at 10 parasites/µL. When extracted donor samples were applied to Pck 5/5 were detected at 100 and 10 parasites/µL. When unextracted donor samples were applied to Ipf 3/5 were detected at 100 parasite/µL, and 0/5 were detected 10 parasites/µL. When extracted donor samples were applied to Ipf 5/5 were detected at 100 parasites/µL, and 4/5 were detected at 10 parasites/µL. When unextracted donor samples were applied to Ptot 0/5 were detected at 100 and 10 parasites/µL. When extracted donor samples were applied to Ptot 5/5 were detected at 100 parasites/µL and 0/5 were detected at 10 parasties/uL. A 4-5 fold difference in signal intensity between the 10 and 100 parasites/µL extracted samples for Pck and Ipf was observed. Generally, all samples of the same parasitemia, analyzed by the same RDT brand, experienced similar enhancements, which seems to point to no individual donor sample effect on the signal.

Example 3—Discussion

The advent and implementation of rapid diagnostic tests have made an invaluable impact on the diagnosis and treatment of infectious diseases in third world countries. The efficacy of these tests at high parasitemia was demonstrated in this study, as all RDT brands analyzed were found to produce detectable signal given unextracted samples at a parasite density of 2000 parasites/µL. (FIG. 6). But as discussions about eradication strategies begin in earnest, the challenge becomes how to effectively identify the untreated asymptomatic patient reservoir. Management of submicroscopic malarial infections has become a challenge in the field, as current rapid diagnostics are unable to detect these patients (Okell et al., 2012; Sturrock et al., 2013; Laishram et al., 2012). Thus, for this study the inventors set their desired detection limit to less than 20 parasites/µL as this will allow for detection of parasite at submicroscopic levels and lead to the diagnosis of more asymptomatic infections (Okell et al., 2012).

The inventors have reached these detection limits through modification of the current DT diagnostic process, which has allowed this method to be simple, rapid and affordable. The RDT diagnostic process was modified by adding a simple sample preparation step, which consists of a self-contained extraction device that purifies and concentrates the malaria biomarker pfHRPII. In order to choose the RDT brands to be evaluated in this study, the WHO report on the performance of all manufactured malaria RDTs was consulted. Given this report, the inventors selected a range of RDT brands representative of low, medium and high performing tests. Because of the nature of their extraction device, the inventors hypothesized that they could improve these tests, regardless of WHO PDS, by application of a small volume of concentrated, purified pfHRPII. Improvement in test performance was benchmarked on changes in the signal intensity of the pfHRPII test line. Analysis of RDT signal as a function of parasitemia from 12.5 to 200 parasites/µL generally pointed to an enhancement in test performance after sample processing as compared to an unextracted sample. Despite the observed enhancement, visual and pixel analysis of the tested brands revealed several brand-to-brand discrepancies. The most noted was in the case of OsPf, where smearing of the sample and RDT components on the test strip increased the background, preventing detection of low parasitemias in this brand (FIG. 7). This failure of the test strip to clear the sample and reagents prevented proper development of the test line and peak identification. Other brand-to-brand differences were observed by comparing the shape of the titration curves. Pck reached saturation in signal intensity after 100 parasites/µL, whereas Ptot and Ipf remained linear through 200 parasites/µL, where this analysis stopped (FIG. 6). These differing trends suggest a greater concentration of active antibody on the test line of Ipf and Ptot RDTs, thus providing a wider linear range for calculations made through the inventors' algorithm.

The multiplicity of enhancement in signal intensity achieved by the extraction of the blood samples was found by comparison of the signal intensity of unextracted and extracted samples at 200 parasites/µL. A minimum 4-fold enhancement was achieved for all tests (FIG. 3). The greatest enhancement was observed for those tests that gave minimal or undetectable results when the samples were unextracted (i.e., Pdip and OsPf). The limits of detection were calculated for all the RDT brand and the enhancement in limits of detection for the various RDT brands followed the same trend as observed for signal enhancement at 200 parasites/µL (FIG. 5). According to the WHO, the limit of detection for malaria RDTs is required to be at least 200 parasites/µL (World Health Organization, 2011). They found five out of six of these brands to have limits of detection ranging from 15-150 parasites/µL given an unextracted sample. OsPf did not detect unextracted samples within the LOD recommended by the WHO. When samples were extracted, the limits of detection were found to be between 3-33 parasites/µL (Table 1). Of the six brands tested, five were enhanced to detect below the set detection limit of 20 parasites/µL, which is representative of asymptomatic and submicroscopic levels of malaria infection. Idual was the only brand tested that was able to detect at this level before extraction. To the inventors' knowledge, no previously developed method for RDT analysis has allowed for the detection of such low parasitemias.

After quantifying the LOD of these brands, the inventors focused the study to three brands (Pck, Ptot and Ipf) analyzing individual donor blood samples to examine the influence of individual donor background. It was found that test performance at 10 and 100 parasites/µL was diagnostic to the individual donor for the three brands evaluated (FIG. 5). Thus, any variations in signal intensity of a given RDT observed for samples with the same preparation and parasitemia were attributed to manufacturing and brand differences. The data collected from this portion of the study was also used to observe trends in RDT performance. An increase in integrated peak area from Pdip to Ipf to Pck was found to correspond to an increase in signal intensity between these brands. This increase in signal followed the trend in the increasing PDS reported by the WHO for these RDT brands (FIG. 4). Although the signal of low and medium performing tests were not enhanced to that of high performing test, enhancement in overall performance was observed across the range of the panel detection scores. Analysis of these three RDT brands also showed that sample extraction reduced the incidence of false negative test results. For example, in the case of Ipf, at 100 parasites/µL, only ⅗ of the unextracted donor samples were detected but upon extraction 5/5 of the donor samples produced detectable signals (FIG. 5). The inclusion of the extraction step makes seemingly bad RDTs work better, by increasing signal and thus reducing false negatives and could be invaluable to malaria management programs to enhance the performance of brands available for use.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

I. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241
Avison, In: *Measuring gene expression*, Taylor & Francis, NY, 2007; 324, 2007.
Bell and Peeling, *Nature Reviews Microbiology*, 4, S34, 2006.

Bell and Perkins, in *Treatment and Prevention of Malaria*, eds. H. M. Staines and S. Krishna, Springer Basel, ch. 15, pp. 293-307, 2012.
Bell et al., *Nat Rev Micro*, 4, 682-695, 2006.
Beuselinck et al., *J. Clinical Microbiol.*, 43(11):5541-5546, 2055.
Chen et al., *Biomed. Microdevices*, 12(4):705-719, 2010.
Coiras et al., *J. Med. Virol.*, 69(1):132-144, 2003.
Davis et al., *Analytical Chemistry*, 84, 6136-6142, 2012.
Gubala et al., *Analytical Chemistry*, 84, 487-515, 2011.
Hagan et al., *Lab. Chip.*, 11(5):957-961, 2011.
Handbook of Solvents, Lide (Ed.), CRC Press, 1-565, 1995.
Laishram et al., *Malaria Journal*, 11, 29, 2012.
*Malaria Rapid Diagnostic Test Performance: Results of WHO product testing of malaria RDTs—Round 3*, World Health Organization, 2011.
Monteiro et al., *J. Clinical Microbiol.*, 35(4):995-998, 1997.
Mudanyali et al., *Lab on a Chip*, 12, 2678-2686, 2012.
Murray and Bennett, *Interdisciplinary Perspectives on Infectious Diseases*, 2009.
Murray et al., *Clinical Microbiology Reviews*, 21, 97-110, 2008.
Niemz et al., *Trends Biotechnol.*, 29(5):240-250, 2011.
Okell et al., *Nat Commun*, 3, 1237, 2012.
Price et al., *Lab. Chip.*, 9(17):2484-2494, 2009.
Radstrom et al., *Mol. Biotechnol.*, 26(2):133-146, 2004.
Shekalaghe et al., *Malaria Journal*, 12, 141, 2013.
Sturrock et al., *PLoS Med*, 10, e1001467, 2013.
Wilson, *Appl. Environ. Microbiol.*, 63(10):3741-3751, 1997.
Wongsrichanalai et al., *The American Journal of Tropical Medicine and Hygiene*, 77, 119-127, 2007.
Yager et al., *Annual Review of Biomedical Engineering*, 2008, 10, 107-144, 2008.
Yamada et al., *J. Virol. Methods*, 27(2):203-209, 1990.
Also VBLT.P0178US
For FIG. 14:
1. Davis, K. M., Swartz, J. D., Haselton, F. R. and Wright, D. W. (2012) Low-Resource Method for Extracting the Malarial Biomarker Histidine-Rich Protein II To Enhance Diagnostic Test Performance. *Analytical Chemistry*, 84, 6136-6142.
2. Davis, K. M., Gibson, L. E., Haselton, F. and Wright, D. (2014) Simple sample processing enhances malaria rapid diagnostic test performance. *Analyst*, 139, 3026-3031.
3. Adams, N. M., Wang, K.-K. A., Caprioli, A. C., Thomas, L. C., Kankia, B., Haselton, F. and Wright, D. (2014) Quadruplex priming amplification for the detection of mRNA from surrogate patient samples. *Analyst*, 139, 1644-1652.
4. Adams, N. M., Bordelon, H., Wang, K.-K. A., Albert, L. E., Wright, D. W. and Haselton, F. R. (2015) Comparison of three magnetic bead surface functionalities for RNA extraction and detection. *ACS applied materials & interfaces*.
5. Cao, W., Easley, C. J., Ferrance, J. P. and Landers, J. P. (2006) Chitosan as a polymer for pH-induced DNA capture in a totally aqueous system. *Analytical chemistry*, 78, 7222-7228.
6. Hagan, K. A., Meier, W. L., Ferrance, J. P. and Landers, J. P. (2009) Chitosan-coated silica as a solid phase for RNA purification in a microfluidic device. *Analytical chemistry*, 81, 5249-5256.
7. Terpe, K. (2003) Overview of tag protein fusions: from molecular and biochemical fundamentals to commercial systems. *Applied microbiology and biotechnology*, 60, 523-533.
8. Gingras, A.-C., Gstaiger, M., Raught, B. and Aebersold, R. (2007) Analysis of protein complexes using mass spectrometry. *Nature reviews Molecular cell biology*, 8, 645-654.
9. Milne, S. B., Tallman, K. A., Serwa, R., Rouzer, C. A., Armstrong, M. D., Marnett, L. J., Lukehart, C. M., Porter, N. A. and Brown, H. A. (2010) Capture and release of alkyne-derivatized glycerophospholipids using cobalt chemistry. *Nature chemical biology*, 6, 205-207.
10. Shin, D.-S., Seo, J. H., Sutcliffe, J. L. and Revzin, A. (2011) Photolabile micropatterned surfaces for cell capture and release. *Chemical Communications*, 47, 11942-11944.
11. Samanta, A., Stuart, M. C. and Ravoo, B. J. (2012) Photoresponsive capture and release of lectins in multilamellar complexes. *Journal of the American Chemical Society*, 134, 19909-19914.
12. Takenaka, T., Endo, M., Suzuki, Y., Yang, Y., Emura, T., Hidaka, K., Kato, T., Miyata, T., Namba, K. and Sugiyama, H. (2014) Photoresponsive DNA Nanocapsule Having an Open/Close System for Capture and Release of Nanomaterials. *Chemistry—A European Journal*, 20, 14951-14954.
13. Li, Q., Tu, X., Ye, J., Bie, Z., Bi, X. and Liu, Z. (2014) Nanoconfining affinity materials for pH-mediated protein capture-release. *Chemical Science*, 5, 4065-4069.
14. Liu, H., Li, Y., Sun, K., Fan, J., Zhang, P., Meng, J., Wang, S. and Jiang, L. (2013) Dual-responsive surfaces modified with phenylboronic acid-containing polymer brush to reversibly capture and release cancer cells. *Journal of the American Chemical Society*, 135, 7603-7609.

What is claimed is:
1. A device comprising:
(a) a first port connected to a first chamber for receiving a removable diagnostic test (RDT) module, wherein said RDT module comprises ports that, when the RDT module is inserted into the device, align with second and third chambers of the device;
(b) a second port connected to the second chamber for receiving a sample, wherein said first and second chambers are in fluid connection, wherein said second port is configured to a receive a tube, such that when said tube is engaged in the second port, said RDT module is locked into said first chamber;
(c) a third port connected to the third chamber for receiving a buffer, wherein said first and third chambers are in fluid connection; and
(d) a magnet.
2. The device of claim 1, wherein said magnet is positioned adjacent to one wall of said first chamber and said second chamber is positioned on an opposite wall of said first chamber.
3. The device of claim 1, wherein said third port is configured to receive a pipette, a tube, or a hose.
4. The device of claim 1, wherein said second port engages a structure on the outer wall of said tube, said structure designed to insure proper positioning of the bottom of said tube in said second chamber.
5. The device of claim 1, wherein said device comprises an perforating element in said second port or chamber such that insertion of said tube results in introduction of an opening in said tube.
6. The device of claim 1, wherein said second and third chambers are connected.

7. A method of performing a diagnostic assay comprising:
(a) introducing a fluid sample suspected of comprising an analyte into a tube that contains magnetic particles carrying a binding ligand for said analyte;
(b) providing the device of claim 1;
(c) introducing said RDT module into said first port connected to said first chamber such that said RDT module is disposed in said first chamber;
(d) introducing said sample mixed with said magnetic particles into said second port connected to said second chamber;
(e) applying a magnetic field to said sample when disposed in said second chamber such that said magnetic particles contact a surface in said RDT module;
(f) introducing a buffer into said third port connected to said third chamber, wherein said buffer contacts a surface in said RDT module and moves toward said second chamber, such that said buffer contacts said magnetic particles disposed on said surface in said RDT module; and
(g) detecting an analyte released from or transported by said magnetic particles by application of said buffer.

8. The method of claim 7, wherein said sample is introduced into said second port and second chamber in said tube, and an opening in said tube is created prior to or during the introduction of said tube into said second port and second chamber.

9. The method of claim 8, wherein said opening is created by removing a portion of said tube or a cap on said tube prior to introduction into said second port, said sample being initially retained in said tube by surface tension at said opening, or wherein the opening is created by introducing said tube into said second port.

10. The method of claim 7, wherein said magnetic field is a static field emanating from said magnet located in said device, or wherein said magnetic field is a user applied field emanating from a magnet inserted into said device or external to said device.

11. The method of claim 8, wherein said second port engages a structure on the outer wall of said tube, said structure designed to insure proper positioning of the bottom of said tube in said second chamber.

12. The method of claim 8, wherein said second and third chambers are connected.

13. The method of claim 7, wherein said analyte is selected from a pathogen antigen, and antibody, an environmental toxin, a drug, or a cancer marker.

14. The method of claim 7, wherein said binding ligand is an antibody, carbohydrate, or a metal.

15. The method of claim 7, wherein said buffer releases said antigen from said magnetic bead by a change in pH, a change in ionic strength, or competitive binding for said ligand or said analyte.

16. The method of claim 15, wherein said buffer further transports said antigen after release into a reaction zone on said RDT module.

17. The method of claim 7, wherein said buffer transports said magnetic particle into a reaction zone on said RDT module.

18. The method of claim 17, further comprising detecting said magnetic particle or an agent located on the surface of said magnetic particle.

* * * * *